US009857291B2

(12) United States Patent
Kwak et al.

(10) Patent No.: US 9,857,291 B2
(45) Date of Patent: Jan. 2, 2018

(54) METROLOGY SYSTEM CALIBRATION REFINEMENT

(71) Applicant: KLA-Tencor Corporation, Milpitas, CA (US)

(72) Inventors: Hidong Kwak, San Jose, CA (US); John Lesoine, San Jose, CA (US); Malik Sadiq, Walnut Creek, CA (US); Lanhua Wei, Fremont, CA (US); Shankar Krishnan, Santa Clara, CA (US); Leonid Poslavsky, Belmont, CA (US); Mikhail M. Sushchik, Castro Valley, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 75 days.

(21) Appl. No.: 14/277,898

(22) Filed: May 15, 2014

(65) Prior Publication Data

US 2014/0340682 A1 Nov. 20, 2014

Related U.S. Application Data

(60) Provisional application No. 61/827,536, filed on May 24, 2013, provisional application No. 61/824,363, (Continued)

(51) Int. Cl.
*G01N 21/21* (2006.01)
*G01N 21/95* (2006.01)
*G01N 21/27* (2006.01)

(52) U.S. Cl.
CPC ......... *G01N 21/211* (2013.01); *G01N 21/274* (2013.01); *G01N 21/9501* (2013.01); *G01B 2210/56* (2013.01); *G01N 2021/213* (2013.01)

(58) Field of Classification Search
CPC .............. G01N 21/211; G01N 21/21; G01N 2021/213; G01N 21/9501;
(Continued)

(56) References Cited

U.S. PATENT DOCUMENTS

| 4,672,196 A * | 6/1987 | Canino ............... G01B 11/065 250/225 |
| 5,581,350 A * | 12/1996 | Chen .................... G01N 21/211 356/369 |

(Continued)

FOREIGN PATENT DOCUMENTS

JP 2007057531 3/2007

OTHER PUBLICATIONS http://www.thefreedictionary.com/measure.*
(Continued)

*Primary Examiner* — Tarifur Chowdhury
*Assistant Examiner* — Mohamed K Amara
(74) *Attorney, Agent, or Firm* — Spano Law Group; Joseph S. Spano

(57) ABSTRACT

Methods and systems for matching measurement spectra across one or more optical metrology systems are presented. The values of one or more system parameters used to determine the spectral response of a specimen to a measurement performed by a target metrology system are optimized. The system parameter values are optimized such that differences between measurement spectra generated by a reference system and the target system are minimized for measurements of the same metrology targets. Methods and systems for matching spectral errors across one or more optical metrology systems are also presented. A trusted metrology system measures the value of at least one specimen parameter to minimize model errors introduced by differing measurement conditions present at the time of
(Continued)

measurement by the reference and target metrology systems. Methods and systems for parameter optimization based on low-order response surfaces are presented to reduce the compute time required to refine system calibration parameters.

21 Claims, 12 Drawing Sheets

Related U.S. Application Data filed on May 16, 2013, provisional application No. 61/838,236, filed on Jun. 22, 2013.

(58) Field of Classification Search
CPC ......... G01N 2021/4792; G01N 21/274; G01N 2021/8848; G01J 4/00; G01J 4/04; G01J 3/0224; G01J 3/447; G01B 11/0641; G01B 11/065; G01B 11/24
USPC ........................................................ 356/369
See application file for complete search history.

(56) References Cited

U.S. PATENT DOCUMENTS

| | | | | |
|---|---|---|---|---|
| 5,798,837 A * | 8/1998 | Aspnes | ............... | G01B 11/0641 356/369 |
| 6,665,070 B1 * | 12/2003 | Yarussi | ................ | G01B 11/272 250/225 |
| 6,949,462 B1 * | 9/2005 | Yang | ..................... | G03F 9/7065 438/650 |
| 7,408,641 B1 * | 8/2008 | Kwak | ................ | G01B 11/0641 356/369 |
| 7,489,399 B1 * | 2/2009 | Lee | .................... | G01B 11/0641 356/369 |
| 7,612,891 B2 * | 11/2009 | Wan | .................... | G01B 11/0675 356/503 |
| 7,990,549 B2 * | 8/2011 | Walsh | .................... | G01B 11/24 356/138 |
| 2004/0073398 A1 | 4/2004 | Nikoonahad et al. | | |
| 2004/0235205 A1 * | 11/2004 | Levy | .................... | G01N 21/211 438/14 |
| 2006/0009872 A1 | 1/2006 | Prager et al. | | |
| 2008/0201095 A1 * | 8/2008 | Yip | ..................... | H01J 49/0009 702/85 |
| 2008/0244348 A1 | 10/2008 | Kadosh et al. | | |
| 2008/0246951 A1 | 10/2008 | Walsh et al. | | |
| 2009/0157343 A1 | 6/2009 | Kaushal et al. | | |
| 2011/0060552 A1 * | 3/2011 | Ono | ........................ | G01B 15/00 702/167 |
| 2011/0246400 A1 * | 10/2011 | Li | .......................... | G01B 11/24 706/12 |
| 2012/0197425 A1 * | 8/2012 | Gross | ................... | G05B 13/042 700/104 |
| 2013/0132021 A1 * | 5/2013 | Kwak | .................. | G01N 21/274 702/104 |
| 2013/0245985 A1 * | 9/2013 | Flock | .................. | G03F 7/70625 702/105 |
| 2013/0325395 A1 * | 12/2013 | Zhou | ....................... | G01B 11/02 702/155 |
| 2015/0324965 A1 * | 11/2015 | Kulkarni | ................... | G06T 7/74 382/144 |
| 2017/0194126 A1 * | 7/2017 | Bhaskar | .................. | H01J 37/06 |
| 2017/0200658 A1 * | 7/2017 | Yang | ..................... | H01L 22/20 |

OTHER PUBLICATIONS

International Search Report and Written Opinion dated Oct. 10, 2014, for PCT Application No. PCT/US2014/038495 filed on May 16, 2014, by KLA-Tencor Corporation, 11 pages.

* cited by examiner

METROLOGY SYSTEM CALIBRATION REFINEMENT

CROSS REFERENCE TO RELATED APPLICATION

The present application for patent claims priority under 35 U.S.C. §119 from U.S. provisional patent application Ser. No. 61/827,536, entitled "Spectral Calibration Refinement (SCR) for CD Matching Improvement," filed May 24, 2013, U.S. provisional patent application Ser. No. 61/824,363, entitled "Spectral Error Matching Based Calibration with Reference Measurement," filed May 16, 2013, and U.S. provisional patent application Ser. No. 61/838,236, entitled "Response Surface Approach to Application-Specific Calibration Refinement For Metrology Devices," filed Jun. 22, 2013. The subject matter of each is incorporated herein by reference in their entireties.

TECHNICAL FIELD

The described embodiments relate to systems for wafer metrology, and more particularly to characterization and defect detection of semiconductor structures and materials.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Optical metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition and other parameters of nanoscale structures.

As devices (e.g., logic and memory devices) move toward smaller nanometer-scale dimensions, characterization becomes more difficult. Devices incorporating complex three-dimensional geometry and materials with diverse physical properties contribute to characterization difficulty. In addition to accurate device characterization, measurement consistency across a range of measurement applications and a fleet of metrology systems tasked with the same measurement objective is also important. If measurement consistency degrades in a manufacturing environment, consistency among processed semiconductor wafers is lost and yield drops to unacceptable levels. Matching measurement results across applications and across multiple systems (i.e., tool-to-tool matching) ensures that measurement results on the same wafer for the same application yield the same result.

A typical calibration approach for model based measurement systems consists of measuring a number of film/substrate systems of known thickness and dielectric function. A regression is performed on machine parameters until the combination of parameters returns the expected values for thickness and/or dielectric function. In one example, a set of film wafers having a silicon dioxide layer on crystalline silicon over a range of thicknesses is measured and a regression is performed on the machine parameters until the machine returns the best match for thickness and/or refraction index for the given set of films. Other examples are described in U.S. Pat. Pub. No. 2004/0073398 entitled, "Methods and Systems for Determining a Critical Dimension and a Thin Film Characteristic of a Specimen," which is incorporated by reference as if fully set forth herein. This calibration procedure may be applied across a fleet of measurement systems using the same set of wafers. These wafers are sometimes referred to as transfer standards.

Machine parameters are often calibrated based on thin film measurements because thin film systems (e.g., silicon dioxide on crystalline silicon) can be manufactured with well known optical constants, clean interfaces, and low surface roughness that enable measurement of wafer characteristics with a degree of repeatability near the sensitivity of the measurement systems being calibrated. However, the accuracy of a metrology system calibrated based on reference wafers is typically limited to wafers with properties that closely match those of the reference wafer. Thus, the effectiveness of calibration based on thin film measurements may be limited in different measurement applications.

To achieve a high level of measurement consistency across a fleet of metrology systems with a reference wafer (or set of reference wafers), calibration experiments involving the reference wafer must be performed in a carefully controlled environment that matches the environmental conditions in place when the reference wafer was originally characterized. This may be difficult to achieve in a manufacturing environment and lead to loss of consistency among metrology systems. In addition, an expensive reference wafer set must be maintained in the manufacturing environment. Risks of wafer breakage or degradation potentially jeopardize the integrity of the calibration process.

Tool-to-tool matching and maintaining tool measurement consistency over time, over maintenance cycles, and over a wide range of measurement applications are core challenges in the development of an optical metrology system that meets customer requirements of the semi-conductor industry. Process and yield control in both the research and development and manufacturing environments demands tool-to-tool consistency of measurement results on the order of the measurement repeatability. Thus, methods and systems for improved tool-to-tool matching and consistent measurement performance over a wide range of measurement applications are desired.

SUMMARY

Methods and systems for matching measurement spectra across one or more optical metrology systems are presented. Such systems are employed to measure structural and material characteristics (e.g., material composition, dimensional characteristics of structures and films, etc.) associated with different semiconductor fabrication processes.

Tool-to-tool matching and measurement consistency over time and over different measurement applications are improved by matching measurement spectra (e.g., $\alpha_{meas}$ and $\beta_{meas}$) across one or more metrology systems, rather than specimen parameter values. More specifically, values of one or more of the subset of system parameters (e.g., $P_{sys1}$)

employed to determine the spectral response of a specimen to a measurement performed by a target metrology system are optimized. The system parameter values are optimized such that differences between measurement spectra generated by a reference system and the target system are minimized for measurements of the same metrology targets. The updated system parameter values are employed in subsequent measurement analyses performed by the target metrology system (e.g., CD measurements, thin-film measurements, CD matching applications, etc.).

In another aspect, methods and systems for matching spectral errors across one or more optical metrology systems are presented. System parameter values of a target metrology system are calibrated based on spectral error matching with a reference metrology system. In addition, at least one specimen parameter value associated with the calibration wafer(s) is measured by a trusted metrology system to minimize model errors introduced by differing measurement conditions present at the time of measurement by the reference and target metrology systems.

In some embodiments, the target metrology system includes two measurement modalities. In these embodiments, the target metrology system includes a first measurement subsystem calibrated such that differences between a spectral error associated with a measurement of a specimen by the target metrology system and a spectral error associated with a measurement of the same specimen by a reference metrology system are minimized. Furthermore, the spectral error associated with the measurement by the target metrology system is determined based at least in part on a parameter of the specimen that is accurately measured by the second measurement subsystem. In this manner, measurement consistency is maintained despite changes in shape of the underlying calibration wafers.

In yet another aspect, methods and systems to perform parameter tuning based on a low-order response surface based optimization are presented. A low-order response surface based optimization reduces the computational burden associated with selecting optimal system parameter values for one or more metrology tools. It is assumed that the response of performance metrics to variations of system parameter values is reasonably approximated by low order polynomials. The low-order response surfaces are constructed using a small number of model evaluations. This significantly reduces the computational resources required to arrive at a refined set of system calibration parameters.

The foregoing is a summary and thus contains, by necessity, simplifications, generalizations, and omissions of detail. Consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Figure 1:
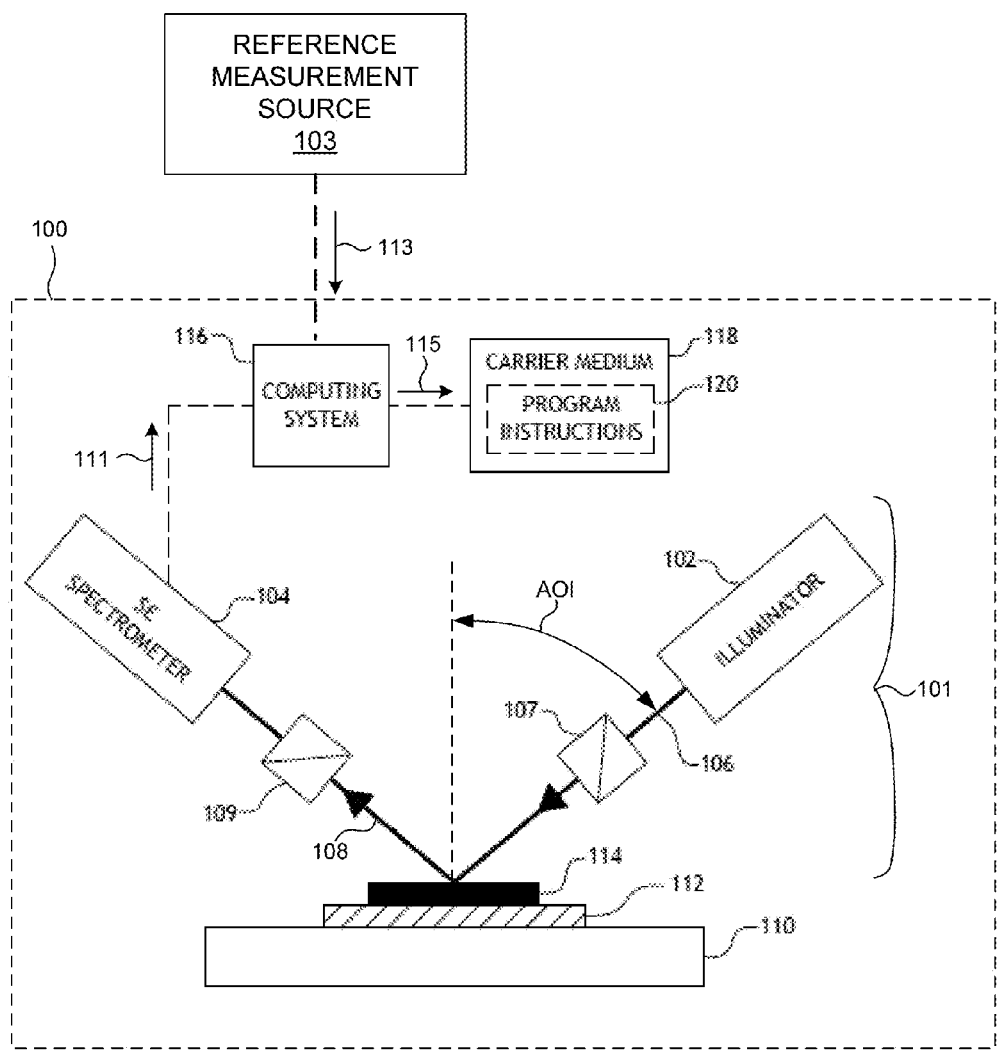
FIG. 1 is a simplified diagram illustrative of a metrology system 100 operable in accordance with the spectral based calibration refinement methods described herein.

FIG. 1 illustrates a metrology system 100 for measuring characteristics of a semiconductor wafer in accordance with the exemplary methods presented herein. As shown in FIG. 1, the system 100 may be used to perform spectroscopic ellipsometry measurements of one or more structures 114 of a semiconductor wafer 112 disposed on a wafer positioning system 110. In this aspect, the system 100 may include a spectroscopic ellipsometer (SE) 101 equipped with an illuminator 102 and a spectrometer 104. The illuminator 102 of the system 100 is configured to generate and direct illumination of a selected wavelength range (e.g., 150-850 nm, 190-850 nm, 240-850 nm, etc.) to the structure 114 disposed on the surface of the semiconductor wafer 112. In turn, the spectrometer 104 is configured to receive illumination reflected from the surface of the semiconductor wafer 112. It is further noted that the light emerging from the illuminator 102 is polarized using a polarization state generator 107 to produce a polarized illumination beam 106. The radiation reflected by the structure 114 disposed on the wafer 112 is passed through a polarization state analyzer 109 and to the spectrometer 104. The radiation received by the spectrometer 104 in the collection beam 108 is analyzed with regard to polarization state, allowing for spectral analysis by the spectrometer of radiation passed by the analyzer. These spectra 111 are passed to the computing system 116 for analysis of the structure 114.

In a further embodiment, the metrology system 100 is a target measurement system 100 that may include one or more computing systems 116 employed to perform calibration of the machine parameter values of the target measurement system 100 in accordance with the methods described herein. The one or more computing systems 116 may be communicatively coupled to the spectrometer 104. In one aspect, the one or more computing systems 116 are configured to receive measurement data 111 associated with a measurement of the structure 114 of specimen 112. In one example, the measurement data 111 includes an indication of the measured spectral response of the specimen by target measurement system 100 based on the one or more sampling processes from the spectrometer 104.

In addition, in some embodiments, the one or more computing systems 116 are further configured to receive measurement data 113 from a reference measurement source 103. In one example, the measurement data 113 includes a set of parameter values associated with a measurement of the structure 114 by a reference metrology system. In some examples, the set of parameter values is stored in carrier medium 118 and retrieved by computing system 116.

It should be recognized that the various elements described throughout the present disclosure may be carried out by a single computer system 116 or, alternatively, a multiple computer system 116. Moreover, different subsystems of the system 100, such as the spectroscopic ellipsometer 101, may include a computer system suitable for carrying out at least a portion of the steps described herein. Therefore, the aforementioned description should not be interpreted as a limitation on the present invention but merely an illustration. Further, the one or more computing systems 116 may be configured to perform any other step(s) of any of the method embodiments described herein. Moreover, some or all of the one or more computing systems 116 may be located remotely from the site of wafer measurement. For example, elements of computing system 116 configured to perform any of the calibration blocks described herein may be located at another facility remotely located from the site of where the wafer is measured.

In this regard, there is no requirement that spectral acquisition and subsequent analysis of the spectral data need be contemporaneous or performed in spatial proximity. For instance, spectral data may be stored in memory for analysis at a later time. In another instance, spectral results may be obtained and transmitted to a computing system located at a remote location for analysis.

In addition, the computer system 116 may be communicatively coupled to the spectrometer 104, the illuminator subsystem 102 of the ellipsometer 101, or the reference measurement source 103 (e.g., an external memory, a reference metrology system, etc.) in any manner known in the art. For example, the one or more computing systems 116 may be coupled to a computing system of the spectrometer 104 of the ellipsometer 101 and a computing system of the illuminator subsystem 102. In another example, the spectrometer 104 and the illuminator 102 may be controlled by a single computer system. In this manner, the computer system 116 of the system 100 may be coupled to a single ellipsometer computer system.

The computer system 116 of the system 100 may be configured to receive and/or acquire data or information from the subsystems of the system (e.g., spectrometer 104, illuminator 102, and the like) by a transmission medium that may include wireline and/or wireless portions. In this manner, the transmission medium may serve as a data link between the computer system 116 and other subsystems of the system 100. Further, the computing system 116 may be configured to receive measurement data via a storage medium (i.e., memory). For instance, the spectral results obtained using a spectrometer of ellipsometer 101 may be stored in a permanent or semi-permanent memory device (not shown). In this regard, the spectral results may be imported from an external system.

Moreover, the computer system 116 may send data to external systems via a transmission medium. The computer system 116 of the system 100 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the computer system 116 and other subsystems of the system 100. Moreover, the computer system 116 may send data to external systems via a transmission medium.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 120 implementing methods such as those described herein may be transmitted over or stored on carrier medium 118. The carrier medium may be a transmission medium such as a wire, cable, or wireless transmission link. The carrier medium may also include a computer-readable medium such as a read-only memory, a random access memory, a solid-state memory, a magnetic or optical disk, or a magnetic tape.

The embodiments of the system 100 illustrated in FIG. 1 may be further configured as described herein. In addition, the system 100 may be configured to perform any other block(s) of any of the method embodiment(s) described herein.

As illustrated in FIG. 1, a beam of broadband radiation from illuminator 102 is linearly polarized in polarization state generator 107, and the linearly polarized beam is then incident on specimen 112. After reflection from specimen 112, the beam propagates toward polarization state analyzer 109 with a changed polarization state. In some examples, the reflected beam has elliptical polarization. The reflected beam propagates through polarization state analyzer 109 into spectrometer 104. In spectrometer 104, the beam components having different wavelengths are refracted (e.g., in a prism spectrometer) or diffracted (e.g., in a grating spectrometer) in different directions to different detectors. The detectors may be a linear array of photodiodes, with each photodiode measuring radiation in a different wavelength range.

In one example, computing system 116 receives the measured data (e.g., raw measurement data) from each detector, and is programmed with software for processing the data it receives in an appropriate manner. The measured spectral response of a specimen may be determined by analyzing the changes in polarization of radiation reflected from the sample in response to incident radiation having known polarization state in any number of ways known in the art.

Any of polarization state generator 107 and polarization state analyzer 109 may be configured to rotate about their optical axis during a measurement operation. In some examples, computing system 116 is programmed to generate control signals to control the angular orientation of polarization state generator 107 and/or polarization state analyzer 109, or other elements of the system 100 (e.g., wafer positioning system 110 upon which specimen 112 rests). Computing system 116 may also receive data indicative of the angular orientation of polarization state analyzer 109 from an analyzer position sensor associated with polarization state analyzer 109. Similarly, computing system 116 may also receive data indicative of the angular orientation of polarization state generator 107 from a polarizer position sensor associated with polarization state generator 107. Computing system 116 may be programmed with software for processing such orientation data in an appropriate manner.

In one embodiment, the polarization state generator 107 is a linear polarizer that is controlled so that it rotates at a constant speed, and the polarization state analyzer is a linear polarizer that is not rotating ("the analyzer"). The signal received at each detector of spectrometer 104 (i.e., the raw measurement data) will be a time-varying intensity given by:

$$I(t)=I_0[1+\alpha \cos(2\omega t-P_0)+\beta \sin(2\omega t-P_0)] \quad (1)$$

where $I_0$ is a constant that depends on the intensity of radiation emitted by illuminator 102, $\omega$ is the angular velocity of polarization state generator 107, $P_0$ is the angle between the optical axis of polarization state generator 107 and the plane of incidence (e.g., the plane of FIG. 1) at an initial time (t=0), and $\alpha$ and $\beta$ are values defined as follows:

$$\alpha=[\tan^2 \Psi-\tan^2(A-A_0)]/[\tan^2 \Psi+\tan^2(A-A_0)] \quad (2)$$

and $$\beta=[2(\tan \Psi)(\cos \Delta)(\tan(A-A_0))]/[\tan^2 \Psi+\tan^2(A-A_0)] \quad (3)$$

where $\tan(\Psi)$ is the amplitude of the complex ratio of the p and s reflection coefficients of the sample and $\Delta$ is the phase of the complex ratio of the p and s reflection coefficients of the sample. The "p" component denotes the component of polarized radiation whose electrical field is in the plane of FIG. 1, and "s" denotes the component of polarized radiation whose electrical field is perpendicular to the plane of FIG. 1. A is the nominal analyzer angle (e.g., a measured value of the orientation angle supplied, for example, from the above-mentioned analyzer position sensor associated with polarization state analyzer 109). $A_0$ is the offset of the actual orientation angle of polarization state analyzer 109 from the reading "A" (e.g., due to mechanical misalignment, $A_0$ may be non-zero).

In general, the spectral response of a specimen to a measurement is calculated by the metrology system based on functions of spectrometer data, S, and a subset of system parameter values, $P_{sys1}$, as illustrated by equations (4) and (5).

$$\alpha_{meas}=m(P_{sys1},S) \quad (4)$$

$$\beta_{meas}=n(P_{sys1},S) \quad (5)$$

The subset of system parameter values, $P_{sys1}$, are those system parameters needed to determine the spectral response of the specimen to the measurement performed by the metrology system.

For the embodiment described with reference to FIG. 1, the subset of system parameters includes the machine parameters of equations (1)-(3). Values of $\alpha_{meas}$ and $\beta_{meas}$ are determined based on a measurement of a particular specimen by metrology system 100 and a subset of system parameter values as described by equations (1)-(3).

In general, ellipsometry is an indirect method of measuring physical properties of the specimen under inspection. In most cases, the measured values (e.g., $\alpha_{meas}$ and $\beta_{meas}$) cannot be used to directly determine the physical properties of the specimen. The nominal measurement process consists of formulating a measurement model that estimates the measured values (e.g., $\alpha_{meas}$ and $\beta_{meas}$) for a given measurement scenario. The measurement model characterizes the interaction of the specimen with the measurement system. The measurement model includes a parameterization of the structure (e.g., film thicknesses, critical dimensions, etc.) and the machine (e.g., wavelengths, angles of incidence, polarization angles, etc.). As illustrated in equations (6) and (7), the measurement model includes parameters associated with the machine ($P_{machine}$) and the specimen ($P_{specimen}$).

$$\alpha_{model}=f(P_{machine},P_{specimen}) \quad (6)$$

$$\beta_{model}=g(P_{machine},P_{specimen}) \quad (7)$$

Machine parameters are parameters used to characterize the metrology tool (e.g., ellipsometer 101), and may include some or all of the subset of system parameters described with reference to equations (4) and (5). Exemplary machine parameters include angle of incidence (AOI), analyzer angle ($A_0$), polarizer angle ($P_0$), illumination wavelength, numerical aperture (NA), etc. Specimen parameters are parameters used to characterize the specimen (e.g., specimen 112 including structures 114). For a thin film specimen, exemplary specimen parameters include refractive index, dielectric function tensor, nominal layer thickness of all layers, layer sequence, etc. For measurement purposes, the machine parameters are treated as known, fixed parameters and the specimen parameters are treated as unknown, floating parameters. The floating parameters are resolved by an iterative process (e.g., regression) that produces the best fit between theoretical predictions and experimental data. The unknown specimen parameters, $P_{specimen}$ are varied and the model output values (e.g., ($\alpha_{model}$ and $\beta_{model}$) are calculated until a set of specimen parameter values are determined that results in a close match between the model output values and the experimentally measured values (e.g., ($\alpha_{meas}$ and $\beta_{meas}$).

In a model based measurement application such as spectroscopic ellipsometry, a regression process (e.g., ordinary least squares regression) is employed to identify specimen parameter values that minimize the differences between the model output values and the experimentally measured values for a fixed set of machine parameter values. Measurement consistency across multiple measurement applications and across multiple tools depends on properly calibrated sets of machine parameter values for each measurement system.

As discussed hereinbefore, an established machine parameter calibration technique for spectroscopic ellipsometers is based on measuring wafers with known specimen parameter values (e.g., known film thickness, dielectric function, CD, etc.) and employing a regression process to identify machine parameter values that minimize the differences between the model output values and the experimentally measured values for the fixed, known set of specimen parameter values. Exemplary methods are described in U.S. Patent Publication No. 2013/0245985 by Klaus Flock et al., the content of which is incorporated herein by reference in its entirety.

The use of targeted CD measurement values to tailor the refinement of system calibration parameters is a computationally intensive process. In addition, since the optimization includes the measurement model (i.e., the model of the interaction between the measurement system and the specimen during measurement) the quality of the measurement model impacts the optimization result.

In one aspect, methods and systems for matching measurement spectra across one or more optical metrology systems are presented. Such systems are employed to measure structural and material characteristics (e.g., material composition, dimensional characteristics of structures and films, etc.) associated with different semiconductor fabrication processes.

In one aspect, methods and systems for matching measurement spectra across one or more optical metrology systems are presented. In the embodiment depicted in FIG. 1, computing system 116 is further configured to determine a value of at least one machine parameter associated with the target measurement system 100 such that measurement spectra generated based on measurements of specimen 112 by target measurement system 100 are matched to measurement spectra generated based on measurements of specimen 112 by a reference metrology system.

Tool-to-tool matching and measurement consistency over time and over different measurement applications are improved by matching measurement spectra (e.g., $\alpha_{meas}$ and $\beta_{meas}$) across one or more metrology systems, rather than specimen parameter values. More specifically, values of one or more of the subset of system parameters (e.g., $P_{sys1}$) employed to determine the spectral response of a specimen to a measurement performed by a target metrology system are optimized. The system parameter values are optimized such that differences between measurement spectra generated by a reference system and the target system are minimized for measurements of the same metrology targets. The updated system parameter values are employed in subsequent measurement analyses performed by the target metrology system (e.g., CD measurements, thin-film measurements, CD matching applications, etc.).

Refining the calibration of system parameters based on matching measured spectra results is a significant improvement in computational speed. In some examples, the optimization of system parameters more than ten times faster than existing methods. In some examples, this enables an on-tool implementation that arrives at refined values of system parameters on-site using computational resources existing on the metrology tool. This, in turn, enables rapid development of best known methods (BKM) in the field. Typically, BKM development involves iterative sets of experiments to arrive at the best tool configuration for various measurement applications. By reducing the computational time associated with a number of system parameters, BKM development time is also reduced.

In general, measured spectra directly correlate to system calibration parameters. Therefore measured spectra include the necessary information to refine the calibration of these system parameters. Moreover, correcting errors introduced by particular system calibration parameter values directly results in more precise SE hardware matching.

Figure 2:
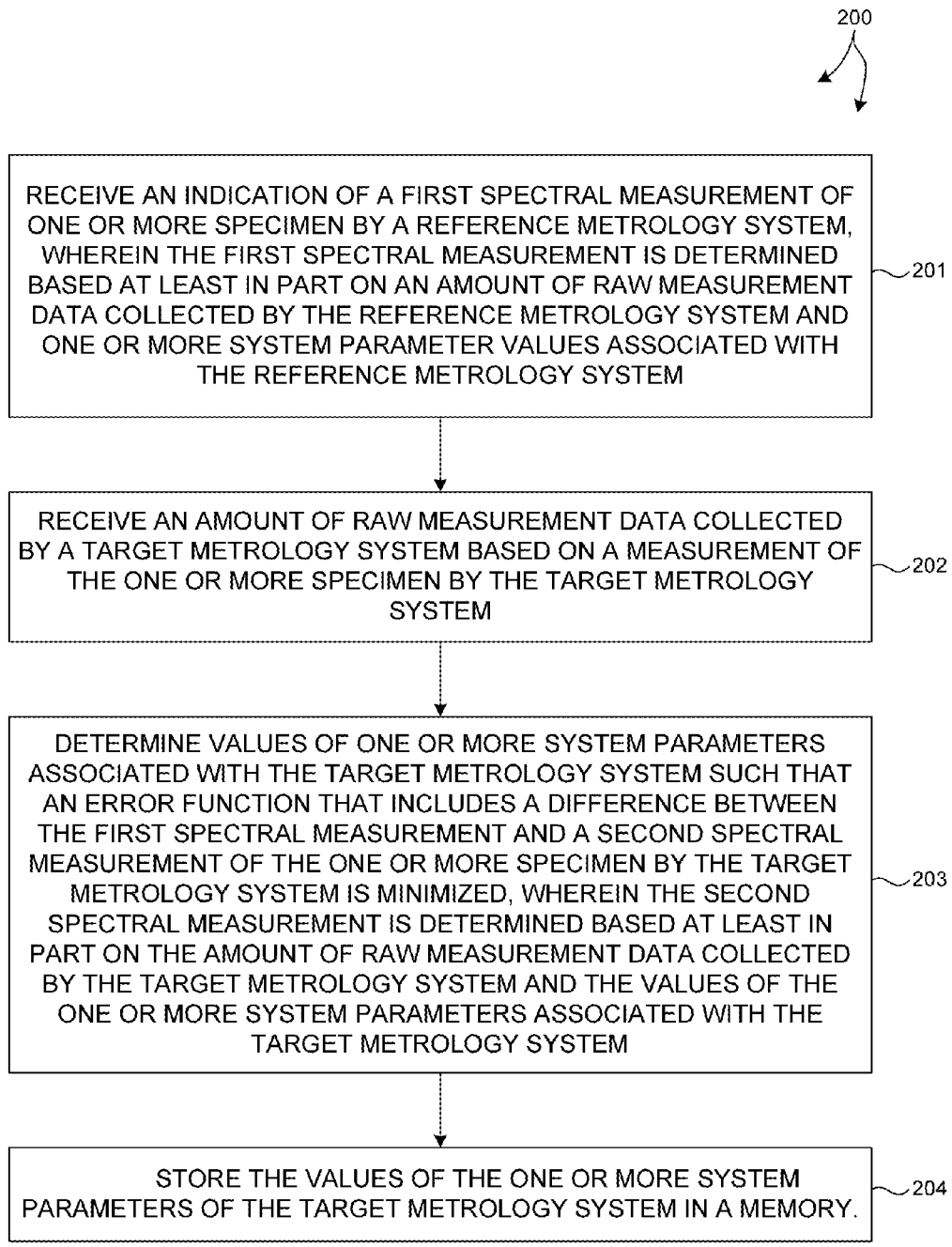
FIG. 2 is a flowchart illustrative of a method 200 of calibrating system parameters of a metrology system to minimize the differences in measured spectra between a target metrology system and a reference metrology system.

FIG. 2 illustrates a method 200 suitable for implementation by the metrology system 100 of the present invention. In one aspect, it is recognized that data processing blocks of method 200 may be carried out via a pre-programmed algorithm executed by one or more processors of computing system 116. While the following description is presented in the context of metrology system 100, it is recognized herein that the particular structural aspects of metrology system 100 do not represent limitations and should be interpreted as illustrative only.

In block 201, an indication of a spectral measurement(s) of one or more specimen by a reference metrology system is received by computing system 116. The spectral measurements are determined based at least in part on an amount of raw measurement data collected by the reference metrology system and one or more system parameter values (e.g., $P_{sys1}$) associated with the reference metrology system. In one example, spectra may be received from a spectroscopic ellipsometer 101. The spectral data may be acquired from structures deposited on the wafer 112 utilizing the spectroscopic ellipsometer 101. For instance, the spectroscopic ellipsometer 101 may include an illuminator 102 and a spectrometer 104, as discussed previously herein. The spectrometer 104 may transmit results associated with a spectroscopic measurement of the structures of the wafer to one or more computing systems 116 for analysis. In another example, spectra may be received from a reflectometer (not shown). In another example, the spectra for the structures may be acquired by importing previously obtained spectral data (e.g., measurement spectra 113 received from reference measurement source 103). In this regard, there is no requirement that the spectral acquisition and the subsequent analysis of the spectral data need be contemporaneous or performed in spatial proximity. For instance, spectral data may be stored in memory for analysis at a later time. In another instance, spectral results may be obtained and transmitted to a computing system located at a remote location for analysis.

In one example, the indications of the measured spectral response are $\alpha_{meas}$ and $\beta_{meas}$ values are derived from measurement data by methods known in the art as discussed hereinbefore with reference to equations (1)-(5). In other examples, other indications of the measured spectral response may be contemplated (e.g., tan $\Psi$ and $\Delta$, etc.). The aforementioned spectral response indications are provided by way of non-limiting example. Other indications or combinations of indications may be contemplated. It is important to note that a spectral indication is based on the spectral response of the specimen, not specific metrics (e.g., film thickness, index of refraction, dielectric constants, etc.) that may be derived from the spectral response of the specimen.

In block 202, an amount of raw measurement data collected by a target metrology system is received by computing system 116. The raw measurement data is generated by the target metrology system based on a measurement of the same one or more specimen as measured by the reference metrology system. In general, the raw measurement data includes the measurement data collected by target measurement system before calculation of measurement spectra. In one example, raw measurement data includes the intensity signals generated by detector elements of spectrometer 104.

In block 203, values of one or more system parameters associated with the target metrology system are determined such that an error function that includes a difference between the spectral measurement of the specimen by the reference metrology system and a spectral measurement by the target metrology system is minimized. The spectral measurement by the target metrology system is determined based at least in part on the amount of raw measurement data collected by the target metrology system and the values of the one or more system parameters associated with the target metrology system. In one example, the spectral measurement of the specimen by the target metrology system is calculated in accordance with equations (1)-(3).

In some examples, a regression is performed on the subset of target system parameters (e.g., Psys1) used to determine the spectral measurement of the specimen by the target metrology system such that an error function is minimized.

The subset of target system parameters subject to optimization may include some or all of the system parameters used to determine a spectral measurement. By way of non-limiting example, these parameters may include any of an analyzer angle offset, A0, polarizer angle offset, P0, a slope coefficient associated with analyzer angle, A, a slope coefficient associated with polarizer angle, P, wavelength calibration coefficients, and point spread function (PSF) calibration coefficients, etc.

An example error function, E, is illustrated in equation (8).

$$E = \sum_{n=0}^{N_\lambda-1} \sum_{i=1}^{N} [\Delta\alpha_i^2(\lambda_n) + \Delta\beta_i^2(\lambda_n)] \quad (8)$$

where, $$\Delta\alpha_i^2(\lambda_n) = (\alpha_{meas_{reference},i} - \alpha_{meas_{target},i})^2 \quad (9)$$

$$\Delta\beta_i^2(\lambda_n) = (\beta_{meas_{reference},i} - \beta_{meas_{target},i})^2.$$

The error function of equation (8) includes the differences in the spectral measurement signals, $\alpha_{meas}$ and $\beta_{meas}$ associated with both the reference metrology system ($\alpha_{measreference}$ and $\beta_{measreference}$) and the target metrology system ($\alpha_{meastarget}$ and $\beta_{meastarget}$) as illustrated in equations (9). The error function is evaluated over each wavelength ($N_\lambda$ wavelengths) sampled at each detector pixel (N pixels).

The error function presented in equation (8) is provided by way of example. Many other error functions may be employed to drive the regression of the target system parameter values. For example, the error function may be weighted by uncertainty in $\alpha$ and $\beta$. In another example, the error function may be the minimization of the maximum value of the difference between the error spectra associated with the reference metrology system and the target metrology system. Other examples may be contemplated based on methods of parameter fitting that are known in the art.

In a further embodiment, the error function driving the regression takes into account the spectral difference at all wavelength sampling points within the wavelength range, for all measurement subsystems, on all measurement sites from all selected samples. An exemplary error function including these elements is illustrated in equation (10).

$$E = \sum_{p=0}^{P-1} \sum_{k=0}^{K_P-1} \sum_{m=0}^{M-1} \sum_{n=0}^{N_\lambda-1} \sum_{i=1}^{N} [\Delta\alpha_i^2(\lambda_n; m, k, p) + \Delta\beta_i^2(\lambda_n; m, k, p)] \quad (10)$$

In this manner, the spectral differences between spectra collected from the reference tool and the target tool are minimized over all measurement samples.

In one example, the spectral difference between the reference metrology system and the target metrology system is measured by the root mean squared error (RMSE) illustrated by equation (11).

$$\text{RMSE} = \frac{1}{\sqrt{2N_\lambda}} \sqrt{\sum_{n=0}^{N_\lambda-1} [\Delta\alpha^2(\lambda_n) + A\beta^2(\lambda_n)]} \quad (11)$$

In yet another example, one or more of the subset of target system parameters (e.g., Psys1) is optimized based on a response surface optimization as further described in this patent document.

In block 204, the values of the one or more system parameters of the target metrology system are stored in a memory. For example, indications 115 of the values of the one or more system parameters of the target metrology system are stored in a memory of carrier medium 118.

The terms reference metrology system and target metrology system generally refer to a metrology system status (i.e., target) that requires adaptation of the system parameters to obtain measurement consistency with another metrology system status (i.e., reference). In this manner, the target is being calibrated with respect to the reference.

In some examples, the target metrology system and the reference metrology system are different tools. For example, in a manufacturing context, it may be advantageous to have a fleet of metrology systems each calibrated to a single reference metrology system. In this manner, each of the fleet of metrology systems is consistent with a single reference tool. In another example, it may be advantageous to have a one or more metrology systems each calibrated to a fleet average of many metrology systems. In this manner, each of the metrology systems is consistent with an entire fleet of metrology tools. In another example, reference and target systems are the same system measured at different times (e.g., before and after a hardware maintenance operation).

In a further aspect, the optimized subset of system parameters is loaded onto the target metrology system. These optimized parameters are subsequently used for further measurement analyses involving the measurement model (e.g., measurement model described with reference to equations (6) and (7). In some examples, critical dimension (CD) measurements are performed by the target measurement system using the optimized subset of system parameters. For example, a structural parameter of the calibration specimen may be estimated based on a regression of the updated target system measurement model on the spectral data associated with the measurement of the calibration specimen. In this example, the spectral data is also calculated based on the underlying raw measurement data and the optimized subset of system parameters.

Similarly, the same structural parameter of the calibration specimen may be estimated based on a regression of the reference system measurement model on the spectral data associated with the measurement of the calibration specimen by the reference system. The differences between the structural parameter values generated by the reference system and the target system can be used to drive an optimization of the system parameters of the target system measurement model. In a preferred embodiment, the subset of system parameters optimized based on spectral matching as described herein are not subjected to additional optimization based on measured structural parameter values (e.g., CD matching, film thickness matching, etc.). However, other system parameters, not included in the subset of system parameters optimized based on spectral matching, may be further optimized based on differences in the estimated values of specimen parameters (i.e., structural or material parameters).

In another further aspect, the error functions driving the optimization of the system parameters can be weighted difference functions that weigh elements of the spectral measurements from the reference and target systems differently. In one example, the relative weightings are based on measurement sensitivity to any of multiple measurement sites, multiple measurement samples, multiple illumination wavelengths, and multiple measurement subsystems. In this manner, specific measurement sites, samples, subsystems, or illumination wavelengths with particularly high measurement sensitivity can be emphasized. In another example, the relative weightings are based on measurement noise associated any of multiple measurement sites, multiple measurement samples, multiple illumination wavelengths, and multiple measurement subsystems. In this manner, specific measurement sites, samples, subsystems, or illumination wavelengths with particularly high measurement noise can be de-emphasized.

Figure 3:
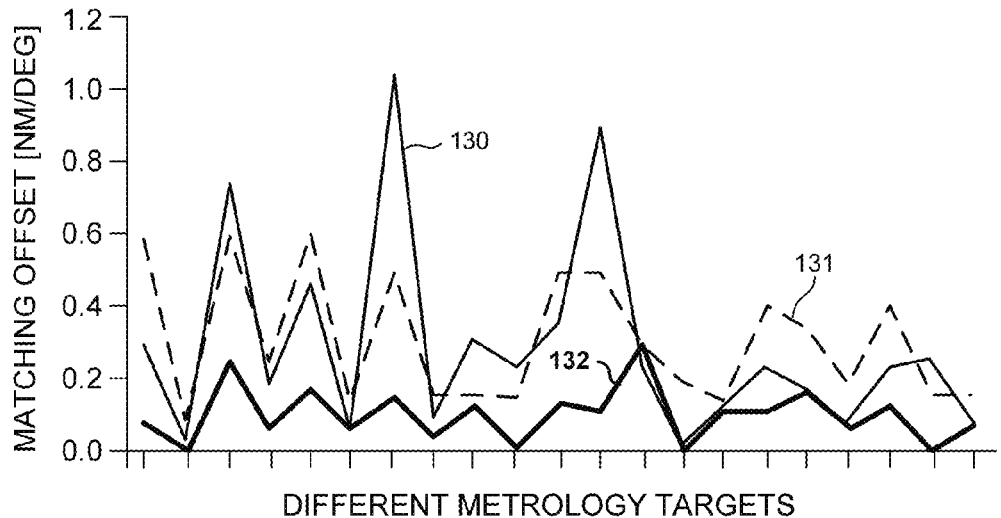
FIG. 3 illustrates a plot comparing specimen parameter matching results between a reference metrology system and a target metrology system before and after spectral based calibration of system parameters.

FIG. 3 illustrates a comparison of specimen parameter matching results between a reference tool and a target tool before and after spectral based calibration of system parameters. The comparison is performed over a number of different metrology targets including CD, SWA, HT, and thickness measurements of several different structures across six different layers. Plotline 131 illustrates a specification for matching of each specimen parameter. Plotline 130 illustrates the match of each specimen parameter before spectral based calibration. As depicted in FIG. 3, the match associated with many of the specimen parameters is outside the specification. Plotline 132 illustrates the match of each specimen parameter after spectral based calibration. As depicted in FIG. 3, the match associated with each specimen parameter is within specification. It should be noted that the results depicted in FIG. 3 illustrate the impact of optimizing system parameter values based on measured spectra only. In other words, the measurement models used to determine estimates of each specimen parameter, both before and after calibration refinement, differ only in the values of the system parameter values optimized based on spectral differences. As described hereinbefore, additional tuning of system parameters may be performed based on matching of specimen parameters to further improve matching performance.

Figure 4:
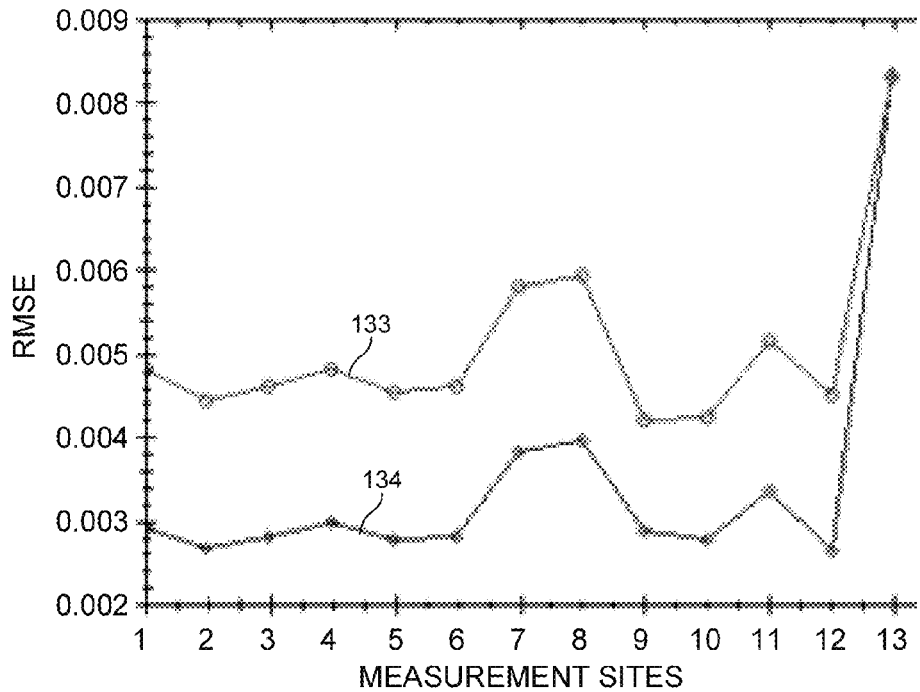
FIG. 4 illustrates a plot comparing the underlying spectral matching improvement corresponding to the CD parameter matching improvement depicted in FIG. 3.

FIG. 4 illustrates a comparison of the underlying spectral matching improvement corresponding to the CD parameter matching improvement depicted in FIG. 3. Plotline 133 illustrates the RMSE (see equation 11) associated with the spectral match between the reference tool and the target tool before spectral based calibration of the system parameters. Plotline 134 illustrates the RMSE associated with the spectral match between the reference tool and the target tool after spectral based calibration of the system parameters.

Figure 5:
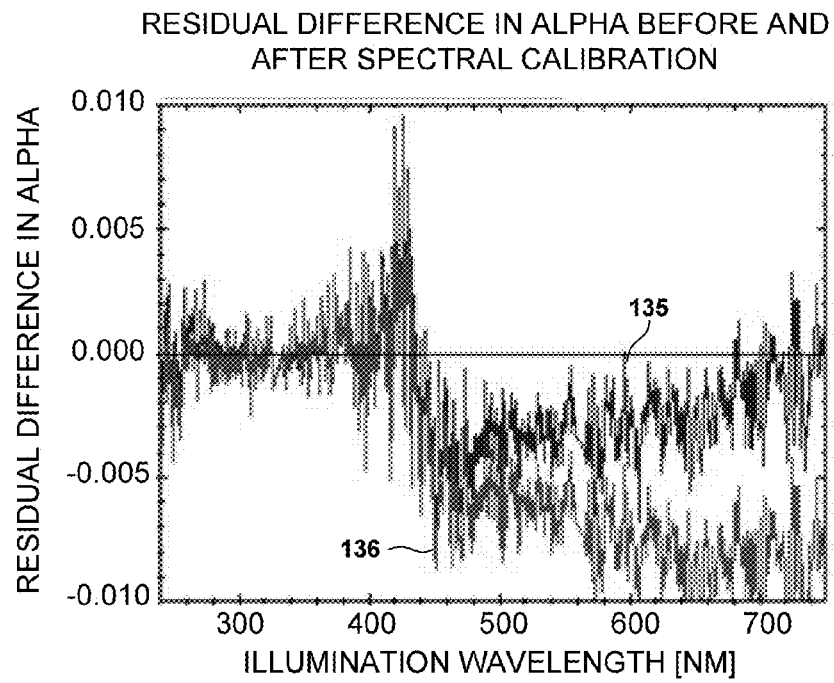
FIG. 5 illustrates a plot comparing the residual difference in $\alpha_{meas}$, before and after spectral based calibration for the first measurement site depicted in FIG. 4.

FIG. 5 illustrates a comparison of the residual difference in $\alpha_{meas}$, before and after spectral based calibration for the first measurement site depicted in FIG. 4. Plotline 136 illustrates the difference between the values of $\alpha_{meas}$ calculated by the reference tool and the target tool over the range of illumination wavelengths before spectral based calibration. Plotline 135 illustrates the difference between the values of $\alpha_{meas}$ calculated by the reference tool and the target tool over the range of illumination wavelengths after spectral based calibration. As depicted in FIG. 5, the differences between the reference tool and the target tool shrink considerably, particularly at longer illumination wavelengths.

Figure 6:
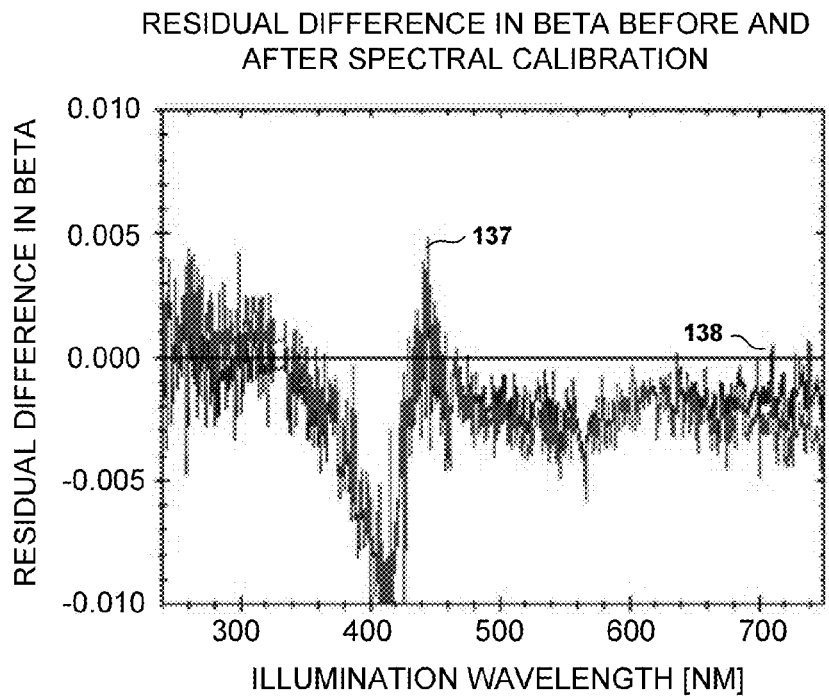
FIG. 6 illustrates a plot comparing the residual difference in $\beta_{meas}$, before and after spectral based calibration for the first measurement site depicted in FIG. 4.

FIG. 6 illustrates a comparison of the residual difference in $\beta_{meas}$, before and after spectral based calibration for the first measurement site depicted in FIG. 4. Plotline 137 illustrates the difference between the values of $\beta_{meas}$ calculated by the reference tool and the target tool over the range of illumination wavelengths before spectral based calibration. Plotline 138 illustrates the difference between the values of $\beta_{meas}$ calculated by the reference tool and the target tool over the range of illumination wavelengths after spectral based calibration. As depicted in FIG. 6, the differences between the reference tool and the target tool shrink after spectral based calibration.

Figure 7:
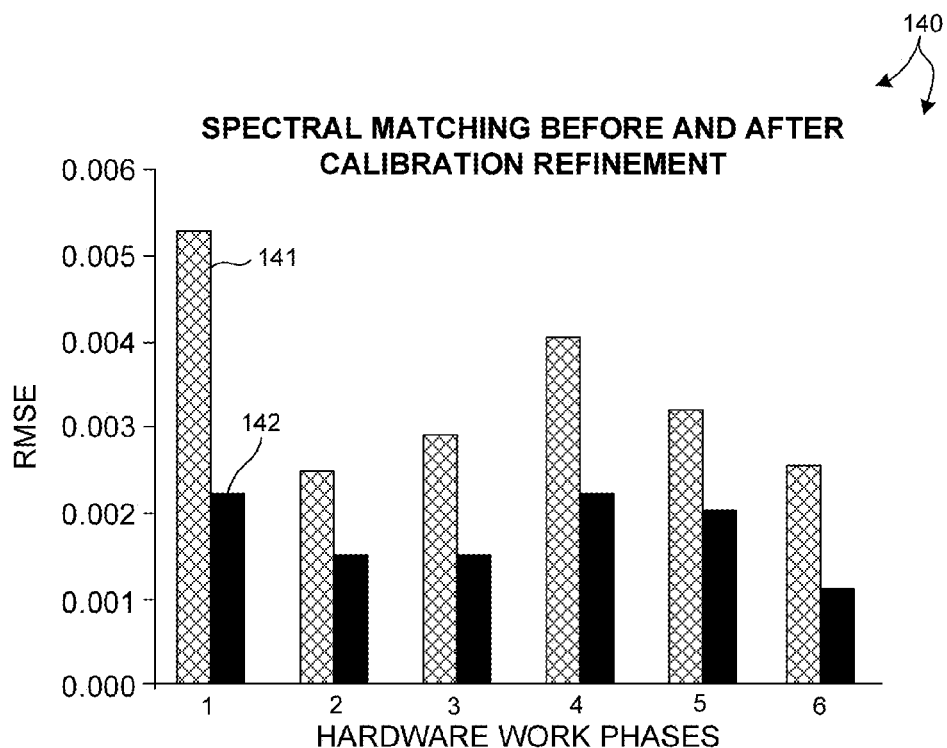
FIG. 7 depicts a plot 140 of the root mean squared error associated with the spectral match between a reference metrology system and a target metrology system after several different hardware work phases.

FIG. 7 depicts a plot 140 of the RMSE (see equation 11) associated with the spectral match between a reference tool and a target tool after several different hardware work phases. In particular, plot 140 illustrates the impact of performing spectral based calibration of the system parameters after hardware work is performed. For example, bar chart indicator 141 illustrates the RMSE associated with the spectral match between a reference tool and a target tool after a particular hardware work phase, but before spectral based calibration is performed. Bar chart indicator 142 illustrates the RMSE associated with the spectral match between the reference tool and the target tool after the same particular hardware work phase, but after spectral based calibration is performed. Similarly, plot 140 illustrates this comparison for several other hardware work phases.

Figure 8:
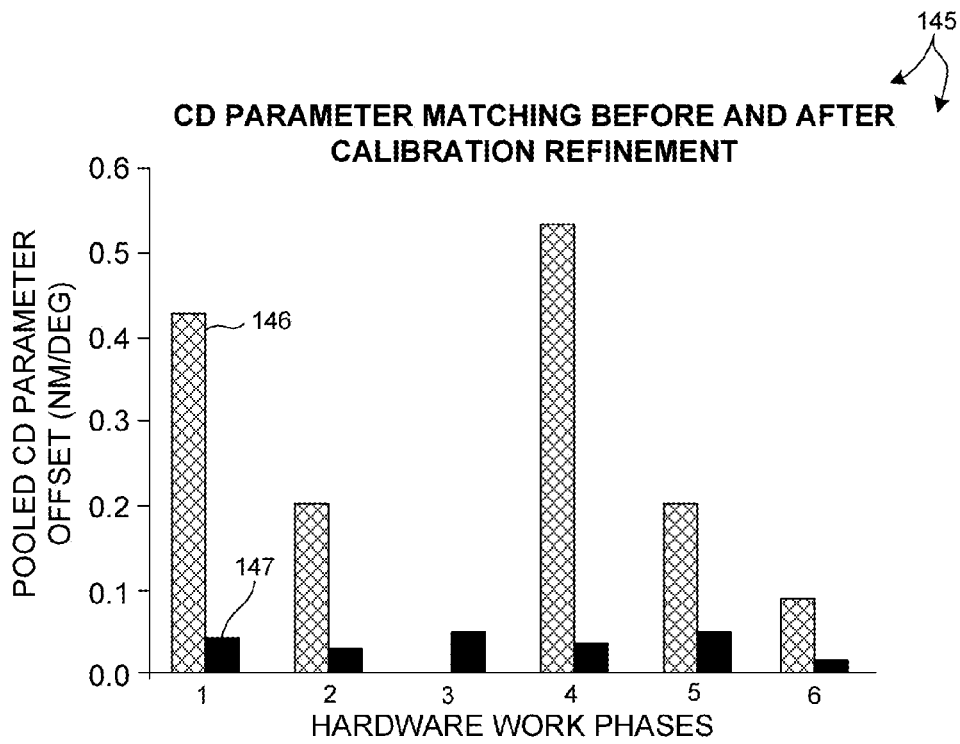
FIG. 8 depicts a plot 145 of the match between a number of CD parameter values estimated by the reference metrology system and the target metrology system after several different hardware work phases.

FIG. 8 depicts a plot 145 of the match between a number of CD parameter values estimated by the reference tool and the target tool after several different hardware work phases. In particular, plot 145 illustrates the impact on the matching of CD measurements by performing spectral based calibration of the system parameters after hardware work is performed. For example, bar chart indicator 146 illustrates the differences associated with the CD match between the reference tool and the target tool after a particular hardware work phase, but before spectral based calibration is performed. Bar chart indicator 147 illustrates the CD match between the reference tool and the target tool after the same particular hardware work phase, but after spectral based calibration is performed. Similarly, plot 140 illustrates this comparison for several other hardware work phases.

As depicted in FIGS. 3-8, calibration refinement of system parameter values based on matching measured spectra results in significant improvements in tool-to-tool matching and measurement stability over a wide range of measurement applications. It should be noted that the application of the aforementioned methods is not limited to spectroscopic ellipsometry. In general, the methods and systems for spectral based calibration refinement may be applied to improve tool-to-tool matching and measurement stability of any spectral measurement tool, in both on-line or off-line implementations. Such systems are employed to measure structural and material characteristics (e.g., material composition, dimensional characteristics of structures and films, etc.) associated with different semiconductor fabrication processes.

Calibration refinement of system parameters based on measured spectra as described herein is based on the assumption that nominal system parameter values are identical and only minor differences need to be calibrated.

To address this limitation, tool-to-tool matching and measurement consistency over time and over different measurement applications are improved by matching spectral errors across one or more metrology systems, rather than specimen parameter values or measured spectra. This approach is described in detail in U.S. Patent Application Publication No. 2013/0132021 by Hidong Kwak et al., the content of which is incorporated herein by reference in its entirety. In this approach system parameter values (e.g., $P_{machine}$) employed as part of the measurement model of a target metrology system are optimized. The system parameter values are optimized such that differences between spectral errors generated by a reference system and the target system are minimized for measurements of the same metrology targets. The updated system parameter values are employed in subsequent measurement analyses performed by the target metrology system (e.g., CD measurements, thin-film measurements, CD matching applications, etc.).

Calibration refinement of system parameters based on spectral error matching is based on fixing specimen parameter values while floating system parameter values to achieve a matching of spectral errors. By fixing specimen parameter values the implicit assumption is that the metrology targets are in the same structural state when measured by the reference system and the target system. However, in many practical situations, this assumption may not hold. For example, if environmental conditions (e.g., temperature, humidity, etc.) or particle contamination levels vary during measurements performed by the reference system and the target system, it should be expected that the size and/or shape of the metrology targets will vary. In another example, if the calibration wafers are somehow lost, broken, or subject to limited availability, a new set of calibration wafers would have to be developed.

In another aspect, tool-to-tool matching and measurement consistency over time and over different measurement applications are improved by matching spectral errors across one or more metrology systems. Furthermore, a reference measurement of at least one specimen parameter value is performed on both the reference tool and the target tool to establish a trusted value of the specimen parameter during each measurement. In this manner, the calibration of system parameters based on spectral errors can be performed while accounting for variations in size and/or shape of the calibration targets. By accounting for these variations, differing environmental conditions during measurement can be accommodated and unavailability of calibration wafers can be accommodated by substituting similar wafers.

Figure 9:
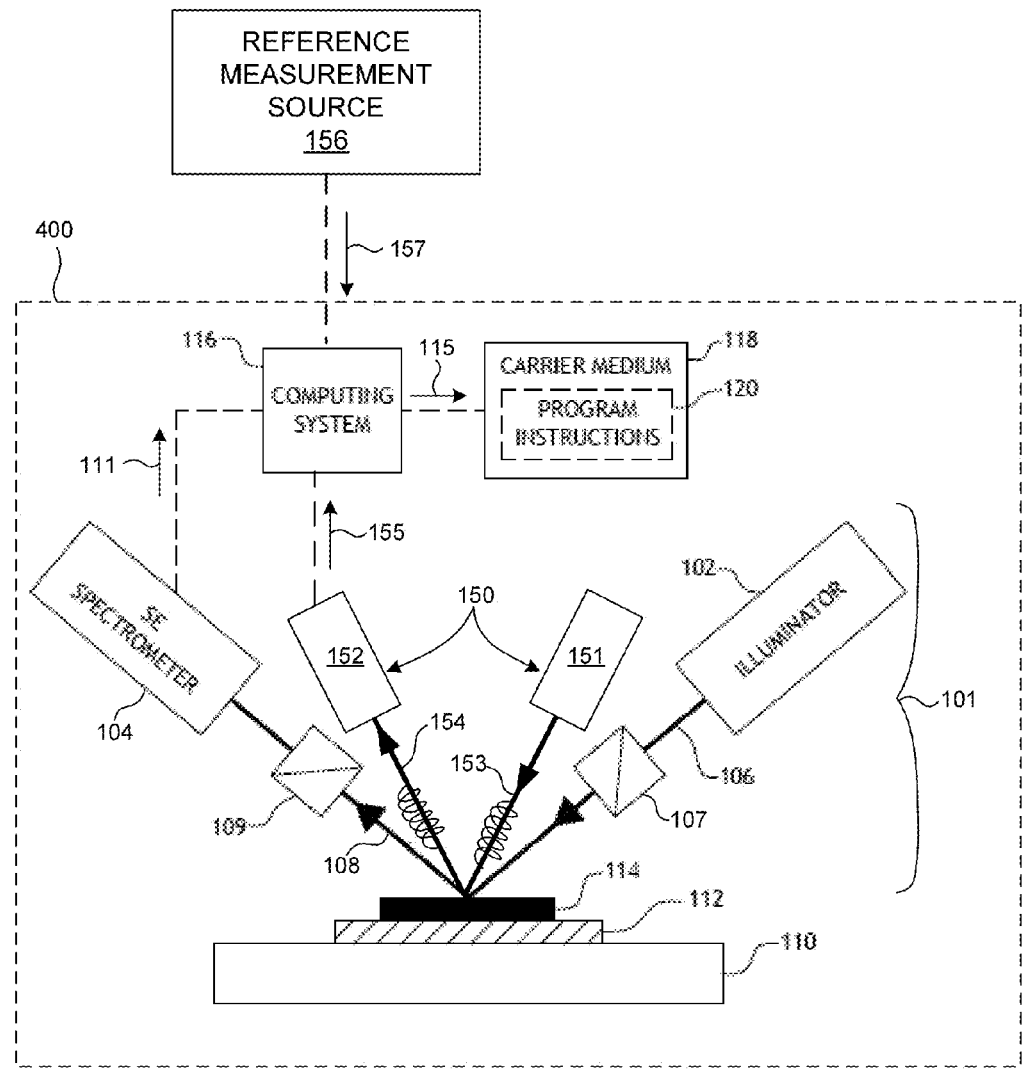
FIG. 9 is a simplified diagram illustrative of a metrology system 400 operable in accordance with the Referenced Spectral Error Based Calibration (rSEBC) methods described herein.

FIG. 9 illustrates a system 400 for measuring characteristics of a semiconductor wafer. System 400 includes like numbered elements analogous to those described with reference to system 100 depicted in FIG. 1. As described with reference to FIG. 1, system 400 may be used to perform spectroscopic ellipsometry on one or more structures 114 of a semiconductor wafer 112 disposed on a wafer positioning system 110. In a further aspect, system 400 includes a single wavelength ellipsometer (SWE) subsystem 150. SWE 150 provides a trusted measurement of at least one specimen parameter, $P_{spec1}$, (e.g., film thickness) that is stable and accurate. SWE 150 includes an illumination source 151 that directs a single wavelength polarized beam 153 to the surface of specimen 114. The reflected beam 154 is collected and analyzed by spectrometer 152. Measured spectra 155 generated by spectrometer 152 are communicated to computing system 116. Additional details regarding single wave ellipsometers are described in U.S. Patent Publication No. 2004/0130718 by Shankar Krishnan, and U.S. Pat. No. 6,734,968 to Haiming Wang et al. The contents of each are incorporated herein by reference in their entirety.

In a further embodiment, system 400 is a target metrology system 400 that may include one or more computing systems 116 employed to perform Referenced Spectral Error Based Calibration (rSEBC) of the target metrology system 400. The one or more computing systems 116 may be communicatively coupled to both spectrometers 104 and 152. In one aspect, the one or more computing systems 116 are configured to receive the results of the one or more sampling processes from the spectrometers. The results include an indication of the measured spectral response of the specimen to measurements by SE 101 and SWE 150.

The one or more computing systems 116 are further configured to determine a specimen parameter (e.g., film thickness) based on the received indication of the measured spectral response of the specimen to measurements by SWE 150.

The one or more computing systems 116 are also configured to determine a spectral error associated with SE 101. In this regard, the computing system 116 determines the spectral error as a difference between the measured spectra and a modeled spectral response of the specimen. From equations (1)-(3), values of $\alpha$ and $\beta$ may be determined based on a measurement of a particular specimen by SE 101 (see equations (4) and (5). Hence, for a particular specimen, values $\alpha_{meas}$ and $\beta_{meas}$ are determined based on spectrometer data. In addition, a measurement model is created that attempts to predict the measured values (e.g., $\alpha_{meas}$ and $\beta_{meas}$). As illustrated in equations (6) and (7), the model includes parameters associated with the system ($P_{machine}$) and the specimen ($P_{specimen}$).

The physical properties of a specimen under inspection are determined by an iterative procedure (e.g., regression). The unknown specimen parameters are varied and the model output values (e.g., $\alpha_{model}$ and $\beta_{model}$) are calculated until a set of specimen parameter determined that results in a close match between the model output values and the experimentally measured values (e.g., $\alpha_{meas}$ and $\beta_{meas}$). The remaining spectral mismatch between the modeled response and the experimentally captured response of the specimen under test is a spectral error. For spectral response values $\alpha$ and $\beta$, the respective spectral errors, $\delta\alpha$ and $\delta\alpha$ are expressed in equations (12) and (13).

$$\delta\alpha = \alpha_{meas} - \alpha_{model} \tag{12}$$

$$\delta\beta = \beta_{meas} - \beta_{model} \tag{13}$$

The one or more computing systems 116 are further configured to receive a spectral error 157 associated with measurements performed by a reference metrology system 156. In some examples, the spectral error associated with the reference metrology system is stored in carrier medium 118 and retrieved by computing system 116. The spectral error associated with the reference metrology system is based on a difference between a measured spectral response and a modeled spectral response of a similar specimen.

In one aspect, system parameter values of a target metrology system 400 are calibrated such that differences between a spectral error associated with a measurement of a specimen by the target metrology system and a spectral error associated with a measurement of a similar specimen by a reference metrology system are minimized. The system parameter values are optimized while fixing the value of at least one specimen parameter (e.g., $P_{spec1}$) measured by a trusted metrology system (e.g., SWE 150). In this manner, rSEBC increases consistency among metrology systems by minimizing the differences in the spectral error among different metrology systems for similar specimen or sets of specimens. System parameters being calibrated are tuned such that the resulting spectral error is close to that of the reference metrology system without modifying specimen parameters. Small inaccuracies in specimen parameter values have little effect on the calibration because they are accounted for by the trusted measurement performed by the trusted measurement system (e.g., SWE 150) present near the reference and target metrology systems.

In addition, by performing rSEBC over a set of specimens with a wide range of specimen parameter values, the resulting calibration is robust to a wide range of measurement applications.

The one or more computer systems are further configured to determine a value of at least one system parameter of the metrology system 400 such that an error function that includes a difference between the spectral error of the target metrology system 400 and the reference metrology system is minimized while fixing the value of at least one specimen parameter to the trusted measurement value. In this respect, a regression process (e.g., ordinary least squares regression) may be employed to identify system parameters of the metrology system that minimize differences between the spectral error associated with the reference metrology system and the spectral error of the target metrology system.

It should be recognized that the various steps described throughout the present disclosure may be carried out by a single computer system 116 or, alternatively, a multiple computer system 116. Moreover, different subsystems of the system 400, such as SE 101 and SWE 150, may include a computer system suitable for carrying out at least a portion of the steps described above. Therefore, the above description should not be interpreted as a limitation on the present invention but merely an illustration. Further, the one or more computing systems 116 may be configured to perform any other step(s) of any of the method embodiments described herein.

As discussed hereinbefore, there is no requirement that the spectral acquisition and the subsequent analysis of the spectral data as described herein need be contemporaneous or performed in spatial proximity. For instance, spectral data may be stored in memory for analysis at a later time. In another instance, spectral results may be obtained and transmitted to a computing system located at a remote location for analysis.

Although, a single wavelength ellipsometer is described as the trusted metrology system with reference to FIG. 9, in general, many other metrology technologies may be employed as the trusted metrology system within the scope of this patent document. For example, any of a beam profile reflectometer, a reflectometer, and an appropriate x-ray based metrology system may be employed as a trusted metrology system.

In addition, there is no requirement that the trusted metrology system be integrated with the target metrology tool. In some examples, the trusted metrology system may be a separate metrology tool. In some embodiments the trusted metrology tool is located at the same facility as the target metrology tool to ensure that the variation in environmental conditions between the time that the specimen 112 is measured on the target system and the trusted system is minimized.

The embodiments of the system 400 illustrated in FIG. 9 may be further configured as described herein. In addition, the system 400 may be configured to perform any other block(s) of any of the method embodiments described herein.

Figure 10:
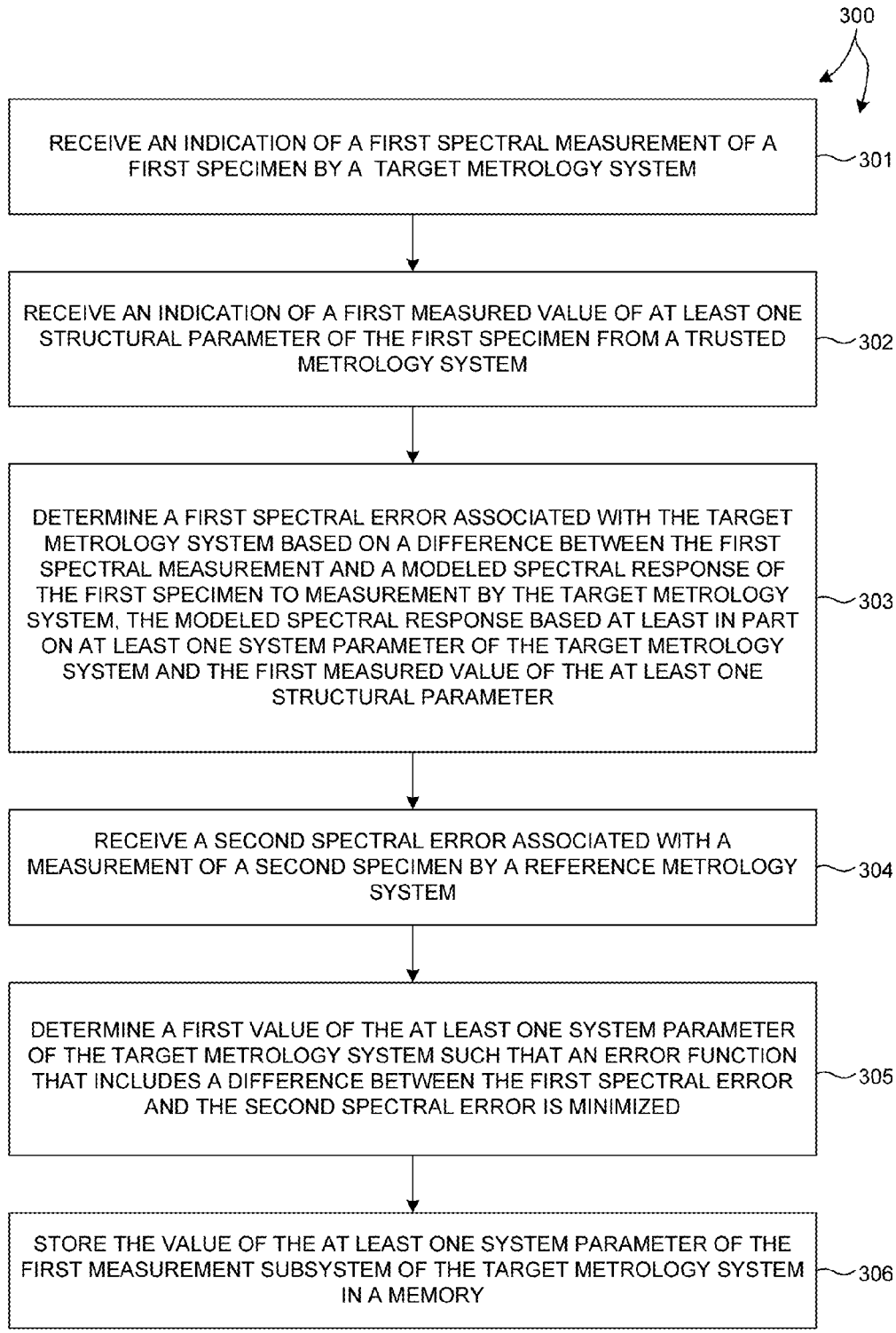
FIG. 10 is a flowchart illustrative of a method 300 of calibrating system parameters of a metrology system to minimize the differences in spectral errors between a target metrology system and a reference metrology system.

FIG. 10 illustrates a method 300 suitable for implementation by the metrology system 400 of the present invention. In one aspect, it is recognized that data processing blocks of method 300 may be carried out via a pre-programmed algorithm executed by one or more processors of computing system 116. While the following description is presented in the context of metrology system 400, it is recognized herein that the particular structural aspects of metrology system 400 do not represent limitations and should be interpreted as illustrative only.

In block 301, an indication of a first spectral measurement of a first specimen is received. The measurement is performed by a target metrology system. In one example, a spectral measurement of specimen 114 by SE 101 is received by computing system 116. In another example, spectra may be received from a reflectometer (not shown).

In one example, the indications of the measured spectral response are $\alpha_{meas}$ and $\beta_{meas}$ values derived from measurement data by methods known in the art as discussed hereinbefore with reference to equations (1)-(3). In other examples, other indications of the measured spectral response may be contemplated (e.g., tan $\Psi$ and $\Delta$, etc.). The aforementioned spectral response indications are provided by way of non-limiting example. Other indications or combinations of indications may be contemplated. It is important to note that a spectral indication is based on the spectral response of the specimen, not specific metrics (e.g., film thickness, index of refraction, dielectric constants, etc.) that may be derived from the spectral response of the specimen.

In block 302, an indication of a first measured value of at least one structural parameter of the first specimen is received from a trusted metrology system. In one example, a spectral measurement of specimen 114 by SWE 150 is received by computing system 116, and a value of a structural parameter of specimen 114 (e.g., film thickness) is determined based on the measurement data provided by SWE 150. In another example, elements of SWE 150 compute the value of the structural parameter directly and communicate the value to computing system 116.

In block 303, a first spectral error associated with measurements by the target metrology system is determined based on a difference between the first spectral measurement and a modeled spectral response of the first specimen to measurement by the target metrology system. The modeled spectral response is based at least in part on at least one system parameter of the target metrology system and the first measured value of the structural parameter measured by the trusted metrology system.

In one example, the spectral error associated with SE 101 is determined by equations (12) and (13). The modeled spectral response (i.e., equations (6) and (7)) includes presumed values of one or more system parameters (i.e., $P_{machine}$) and a trusted value of the specimen parameter (i.e., film thickness) measured by SWE 150.

In block 304, a second spectral error associated with a measurement of a second specimen by a reference metrology system is received by computing system 116. The second spectral error is determined in a manner analogous to the first spectral error, except the second spectral error is based on spectral data measured by the reference metrology system, and the trusted specimen parameter value(s) are measured by a trusted metrology system proximately located to the reference metrology system. Similarly, there is no requirement that the trusted metrology system be integrated with the reference metrology tool. In some examples, the trusted metrology system may be a separate metrology tool. In some embodiments the trusted metrology tool is located at the same facility as the reference metrology tool to ensure that the variation in environmental conditions between the time that the specimen 112 is measured on the reference system and the trusted system is minimized.

In some examples, the second specimen is the same as the first specimen, only measured at a different time. In addition, as discussed hereinbefore, the reference metrology system and the target metrology system can be the same or different systems.

In block 305, a value of at least one system parameter of the first measurement subsystem of the target metrology system is determined such that an error function that includes a difference between the first spectral error and the second spectral error is minimized. In one example, computing system 116 performs a regression analysis to solve for one or more system parameters such that the error function, E, illustrated in equation (14), is minimized.

$$E = \sum_{i=1}^{N} [(\delta\alpha_{T,i}(P_{sys}) - \delta\alpha_{R,i})^2 + ((\delta\beta_{T,i}(P_{sys}) - \delta\beta_{R,i})^2)] \quad (14)$$

Error function, E, is a least squared error function that includes the sum of the squares of each of the differences between the spectral error of the target metrology system (e.g., $\delta\alpha_T$ and $\delta\beta_T$) and the reference metrology system (e.g., $\delta\alpha_R$ and $\delta\beta_R$) over each of the captured pixels (N pixels) for both $\alpha$ and $\beta$. The analysis is performed while the specimen parameter value measured by SWE 150 of the target measurement system is held fixed to its measured value during each iteration of the underlying model calculation of modeled spectral error associated with SE 101.

The error function presented in equation (14) is provided by way of example. Many other error functions may be employed to drive the regression of the system parameter values. For example, the error function may be weighted by uncertainty in $\alpha$ and $\beta$. In another example, the error function may be the minimization of the maximum value of the difference between the error spectra associated with the reference metrology system and the target metrology system. Other examples may be contemplated based on methods of parameter fitting that are known in the art.

In some examples, one or more of the system parameter of the target metrology system (e.g., Psys1) are optimized based on a response surface optimization as further described in this patent document.

In block 306, the value of the at least one system parameter of the first measurement subsystem of the target metrology system is stored in a memory.

The terms reference metrology system and target metrology system generally refer to a metrology system status (i.e., target) that requires adaptation of the system parameters to obtain measurement consistency with another metrology system status (i.e., reference). In this manner, the target is being calibrated with respect to the reference. In some examples, the target metrology system and the reference metrology system are different tools. For example, in a manufacturing context, it may be advantageous to have a fleet of metrology systems each calibrated by rSEBC with respect to a single reference metrology system. In this manner, each of the fleet of metrology systems is consistent with a single reference tool.

In some other examples, the target metrology system and the reference metrology system are the same tool performing measurements at different times. For example, rSEBC may be performed as a diagnostic of the health of a particular metrology system. If the spectral error match associated with measurements of a set of calibration wafers degrades over time, it may be an indication that the hardware of the metrology system is compromised and must be repaired to return to active service. Similarly, rSEBC may be performed periodically on an individual metrology system to maintain measurement stability over time. For example, over time the physical characteristics of a particular metrology system may drift. By running rSEBC periodically, the metrology system may be recalibrated to compensate for drift over time. In this scenario, the reference metrology system is the metrology system in a physical state at a time when a particular wafer was inspected. The target metrology system is the same metrology system in a changed physical state (e.g., after drift has occurred) at a later time when the same (or similar) wafer is inspected again. In this manner, rSEBC may be performed to recalibrate the system parameters of the metrology system to ensure that the measurement behavior is consistent with measurement behavior of the same tool at an earlier time (e.g., when the tool was initially calibrated.).

In another example, rSEBC may be performed before and after any preventative maintenance operation is performed on a particular metrology system. Periodically, a metrology system must be partially disassembled to perform preventative maintenance. When the metrology system is reassembled, the physical characteristics of the system are changed. SEBC may be performed to recalibrate the system to recover the measurement performance of the system before preventative maintenance was performed. In this manner, the reference metrology system is the metrology system in a physical state before the preventative maintenance operation and the target metrology system is the metrology system in a changed physical state after preventative maintenance.

Figure 11:
FIG. 11 illustrates a chart 160 indicative of an improvement in measurement consistency before and after preventative maintenance operations are performed on a particular metrology system by implementing rSEBC for SE measurements performed over illumination wavelengths ranging from 190 nanometers to 850 nanometers.

FIG. 11 illustrates a chart 160 indicative of an improvement in measurement consistency before and after preventative maintenance operations are performed on a particular metrology system by implementing rSEBC for SE measurements performed over illumination wavelengths ranging from 190 nanometers to 850 nanometers. As illustrated in FIG. 11, the first column shows the nominal thickness of the measured layers. As illustrated in FIG. 11, structures having different oxide layer thicknesses are measured. The second column shows a series of layer thickness measurements performed by a reference metrology system. The third column illustrates the results of the same series of thickness measurements on the same wafer by a target metrology system without performing rSEBC. The difference between the two measurements is illustrated in the fourth column. The fifth column illustrates the results of the same series of thickness measurements on the same wafer by the target metrology system after performing rSEBC as described herein. The differences between the thickness measurements by the target metrology system after calibration and the reference metrology system are illustrated in the sixth column. As illustrated by the smaller differences in sixth column, the measurement consistency between the target metrology system and the reference metrology system is significantly improved by implementing rSEBC.

Figure 12:
FIG. 12 illustrates a chart 165 indicative of an improvement in measurement consistency before and after preventative maintenance operations are performed on a particular metrology system by implementing rSEBC for SE measurements performed over illumination wavelengths ranging from 240 nanometers to 850 nanometers.

FIG. 12 illustrates a chart 165 indicative of an improvement in measurement consistency before and after preventative maintenance operations are performed on a particular metrology system by implementing rSEBC for SE measurements performed over illumination wavelengths ranging from 240 nanometers to 850 nanometers. As illustrated in FIG. 12, the first column shows the nominal thickness of the measured layers. As illustrated in FIG. 12, structures having different oxide layer thicknesses are measured, along with a thick nitride layer, and a multi-layer film stack including a nitride and oxide layers. The second column shows a series of layer thickness measurements performed by a reference metrology system. The third column illustrates the results of the same series of thickness measurements on the same wafer by a target metrology system without performing rSEBC. The difference between the two measurements is illustrated in the fourth column. The fifth column illustrates the results of the same series of thickness measurements on the same wafer by the target metrology system after performing rSEBC as described herein. The differences between the thickness measurements by the target metrology system after calibration and the reference metrology system are illustrated in the sixth column. As illustrated by the smaller differences in sixth column, the measurement consistency between the target metrology system and the reference metrology system is significantly improved by implementing rSEBC.

By matching spectral errors between metrology systems rather than measured spectra, metrology systems with different system parameter values may be calibrated to deliver consistent measurement results. For example, a metrology system with an angle of incidence of sixty five degrees may be calibrated to deliver measurement results that are consistent with an metrology system with an angle of incidence of seventy degrees.

Figure 13:
FIG. 13 illustrates a chart 170 indicative of an improvement in measurement consistency before and after preventative maintenance operations are performed on a particular metrology system by implementing rSEBC for SE measurements.

FIG. 13 illustrates a chart 170 indicative of an improvement in measurement consistency before and after preventative maintenance operations are performed on a particular metrology system by implementing rSEBC for SE measurements. In this example, the reference system has an angle of incidence of sixty five degrees while the target system has an angle of incidence of seventy degrees. As illustrated in FIG. 13, the first column shows the nominal thickness of the measured layers. Structures having different oxide layer thicknesses are measured, along with a thick nitride layer, and a multi-layer film stack including a nitride, oxide, and polyamide layers. The second column shows a series of layer thickness measurements performed by a reference metrology system. The third column illustrates the results of the same series of thickness measurements on the same wafer by a target metrology system without performing rSEBC. The difference between the two measurements is illustrated in the fourth column. The fifth column illustrates the results of the same series of thickness measurements on the same wafer by the target metrology system after performing rSEBC as described herein. The differences between the thickness measurements by the target metrology system after calibration and the reference metrology system are illustrated in the sixth column. As illustrated by the smaller differences in sixth column, the measurement consistency between the target metrology system and the reference metrology system is significantly improved by implementing rSEBC.

As illustrated in these examples, rSEBC increases the measurement consistency before and after a preventative maintenance operation. Furthermore, system recovery time is reduced (by minimizing the need to engage in additional calibration operations), and in some cases, maintains the system baseline and correlations without additional calibration effort.

Furthermore, these examples illustrate an improvement in measurement consistency over a range of physical characteristics of a specimen. As illustrated in FIGS. 11-13, different wafers, each having a different nominal oxide layer thickness, are measured by the metrology system. The nominal oxide layer thickness of each wafer is illustrated in the first column. An improvement in measurement consistency is demonstrated for a number of different wafers, each having a different oxide layer thickness. Measurement results for wafers with a large range of oxide layer thickness (30 Angstroms to 9000 Angstroms) are illustrated. Measurement consistency for each of oxide layer thicknesses is significantly improved by implementing rSEBC as described herein.

The embodiments described herein generally relate to methods for increasing consistency among metrology systems by minimizing the differences in the spectral error among different metrology systems for similar specimens or sets of specimens. System parameter values of a target metrology system are calibrated such that the difference between a spectral error associated with a measurement of a specimen by the target metrology system and a spectral error associated with a measurement of a similar specimen by a reference metrology system is minimized. For example, one embodiment relates to a computer-implemented method for minimizing the differences in the spectral error among different metrology systems for similar specimens or sets of specimens based on spectroscopic ellipsometer data. However, the methods described herein are not limited in the types of metrology systems from which spectral error may be derived. For example, in one embodiment, the metrology system includes a reflectometer for thin film metrology of the wafer.

As described herein, rSEBC may be applied to one or more metrology systems in addition to other calibration methods. In some examples, each metrology system may be individually calibrated using known techniques and then rSEBC may be applied to increase consistency among a group of metrology systems.

Many semiconductor metrology techniques involve measurement models that attempt to accurately describe the interaction of the specimen with the metrology system. Such a model is described hereinbefore with reference to SE 101. The measurement model includes system parameters (e.g., $P_{machine}$) that must be calibrated to achieve a particular specification of one or more measurement performance metrics (e.g., measurement precision, measurement accuracy, spectral matching, spectral error matching, CD matching, etc.) Typically, a metrology system manufacturer performs an initial calibration to achieve a general specification of various performance metrics over a wide range of measurement applications. However, in practice, the calibration parameters are further refined to achieve more stringent performance objectives, albeit over a more narrow range of applications. This process is often termed "application-specific calibration." In general, calibration parameters may be optimized for individual performance (e.g., precision, accuracy, etc.) as well as for tool-to-tool performance (e.g., spectral matching, spectral error matching, CD matching, etc. between two tools or a fleet of tools).

Application-specific calibration methods typically define a design of experiment (DOE), i.e., a set of measurement targets that spans the range of measurement applications under consideration. Specifications for measurement performance metrics are also defined. Measurement data (e.g., measured spectra) is collected for each DOE target. Typically, a cost function is constructed based on the performance metrics and some sort of iterative optimization method is employed to compute the optimal values of calibration parameters.

As described hereinbefore, in some examples, spectral based calibration refinement and rSEBC are involve iteration on a cost function to arrive at an optimal set of system parameter values. The objective is to arrive at a set of system parameter values that realizes the closest spectral match and the closest spectral error match, respectively over the measurement application range under consideration.

Processing a single measurement data point is computationally demanding, as it involves multiple numerical evaluations of the measurement models. Optimization techniques that involve blindly searching through parameter space (e.g., grid or step based optimization methods) require a very large number of model evaluations, particularly as the number of calibration parameters grows. The problem is further aggravated if a single calibration setting cannot accomplish the desired performance for the entire collection of measurement applications. In this case each individual application may need its own calibration. In the case of fleet matching, optimization must be performed for calibration parameters for all devices simultaneously. This results in an extremely high-dimensional optimization space.

As the number of system parameter values and the number of tools over which the performance requirements must be met increases, the computational burden associated with an iterative regression procedure involving blind optimization greatly increases.

In one aspect, a low-order response surface approach to optimization of system parameters is employed to reduce the computational burden associated with selecting optimal system parameter values for one or more metrology tools. It is presumed that all system parameters subject to application-specific calibration have been previously calibrated using a factory generic calibration method. Hence, an application-specific refinement of the existing calibration results in a relatively small change in system parameter values. Thus, it is assumed that the response of performance metrics to variations of system parameter values is reasonably approximated by low order polynomials. The low-order response surfaces are constructed using a small number of model evaluations. This significantly reduces the computational resources required to arrive at a refined set of system calibration parameters.

Figure 14:
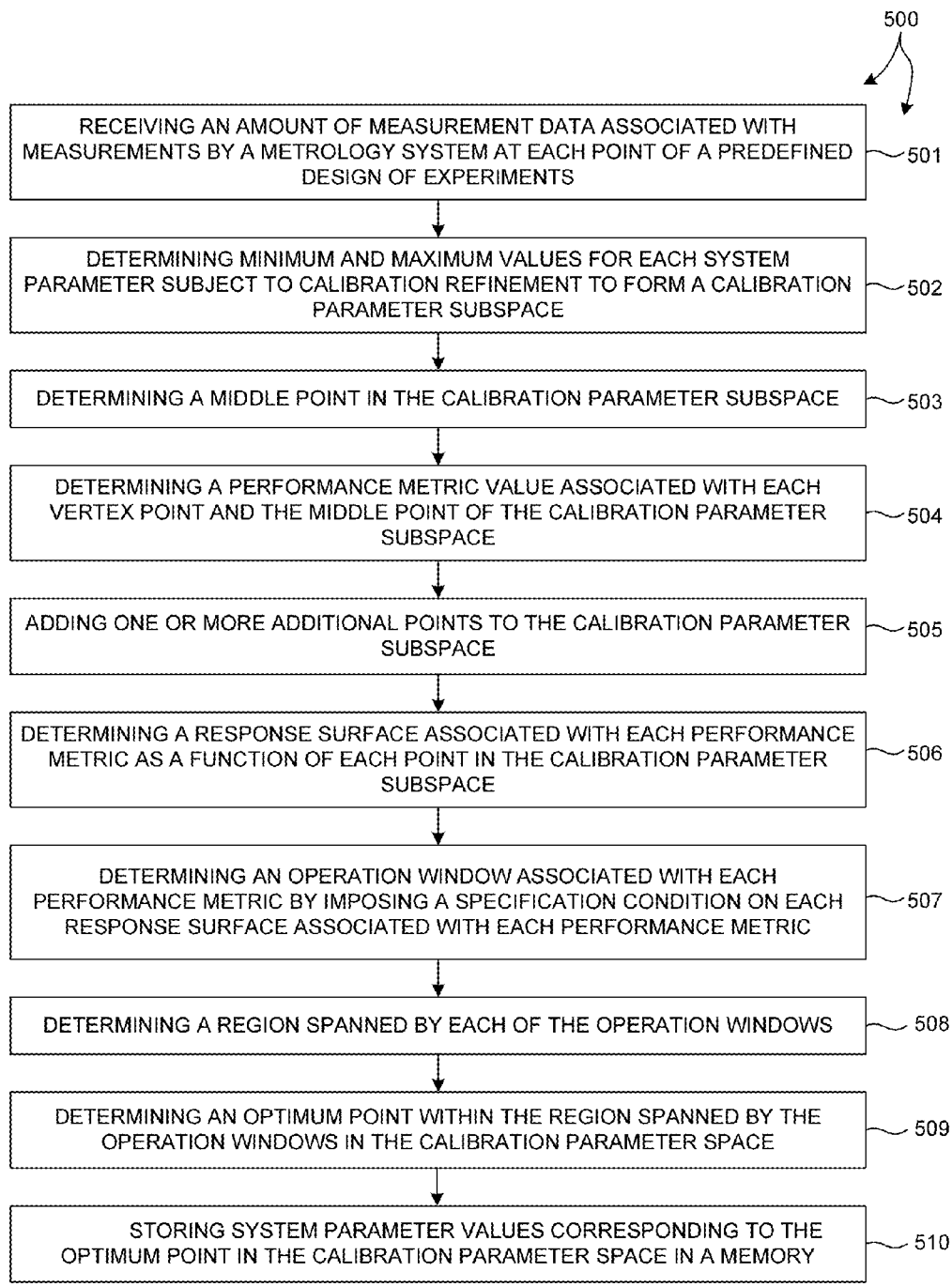
FIG. 14 is a flowchart illustrative of a method 500 of calibration of system parameters based on low-order response surfaces.

FIG. 14 illustrates a method 500 of calibration of system parameters based on low-order response surfaces that is suitable for implementation by metrology systems 100 and 400. In one aspect, it is recognized that data processing blocks of method 500 may be carried out via a pre-programmed algorithm executed by one or more processors of computing system 116. While the following description is presented in the context of metrology systems 100 and 400, it is recognized herein that the particular structural aspects of metrology systems 100 and 400 do not represent limitations and should be interpreted as illustrative only.

In block 501, an amount of measurement data associated with measurements by a metrology system at each point of a predefined design of experiments is received by computing system 116.

In block 502, minimum and maximum values are determined for each system parameter subject to calibration refinement. In a multi-parameter calibration example, these ranges of values form a calibration parameter subspace (i.e., a hypercube in calibration parameters space).

In block 503, the middle of the calibration parameter subspace (i.e., the middle of the hypercube) is determined. In some examples, this is referred to as factorial design with centerpoints.

In block 504, the performance metrics are evaluated at the vertices and middle point of the calibration parameter subspace.

In an optional block, calibration parameters that have an insignificant impact on overall performance are eliminated. The elimination of calibration parameters is optional. However, in some examples, it may be preferable to eliminate relatively inconsequential system parameters before proceeding to more computationally intensive elements of this procedure.

In block 505, points are added to the calibration parameter subspace. In some examples points are added in the calibration hyperspace to form a central composite design pattern.

In block 506, a response surface associated with each performance metric is determined as a function of each point in the calibration parameter subspace. Each response surface approximates the values of each performance metric at each point in the calibration parameter subspace. In some examples, a quadratic polynomial model is determined for each performance metric as a function of calibration parameters using the performance metric values at all points in the DOE. In some examples, the quadratic polynomial model is determined by a linear least squares approximation. The goodness of fit can be checked to ensure model quality. In some other examples a higher order response surface may be contemplated. Considering each performance metric individually, the response surface is defined by a scalar function (i.e., performance metric values) of a vector argument (i.e., calibration parameters).

In block 507, an operation window associated with each performance metric is determined by imposing a specification condition on each response surface associated with each performance metric. For a particular response surface associated with an individual performance metric, the specification condition defines a horizontal cross section of the response surface. This defines the operation window of calibration parameter values that satisfy for the specification for each performance metric. In this manner, operational windows are defined for each performance metric.

In block 508, the region spanned by all operation windows is determined.

In block 509, an optimum value is determined within the region spanned by the operation windows. In some examples, the optimum value is determined as the middle point, i.e., the point in calibration parameter space that is furthest from each of the operational window boundaries. In another example, the optimum point is determined based on a composite criterion, such as a weighted cost function of all individual performance metrics. In this example, the optimum calibration can be found based on the already constructed quadratic response surface approximation. If needed, calibration can be further refined by performing some form of analytical or numeric optimization.

In block 510, the system parameter values corresponding to the optimum point in the calibration parameter space are stored in a memory (e.g., carrier medium 118).

In one example, a fleet of metrology systems based on spectrum ellipsometer (SE) technology (e.g., systems 100 and 400) are calibrated to meet specified performance metrics in accordance with method 500. Each metrology system runs a set of measurement recipes. Each measurement recipe includes a set of measured parameters (i.e., specimen parameters), M. A specification is defined for measurement precision for each parameter, M, for each recipe. In addition, a matching specification is defined for measurements from the fleet of metrology systems. The matching specification is also defined for each measured parameter, M, for each recipe.

The process of narrowing the operational window to meet the precision and matching requirements is described for two metrology systems (Tool A and Tool B), one recipe, and one calibration parameter (CD measurement angle) for purposes of illustration. In general, the methods described herein apply to any number of metrology systems, recipes, and calibration parameters.

Figure 15:
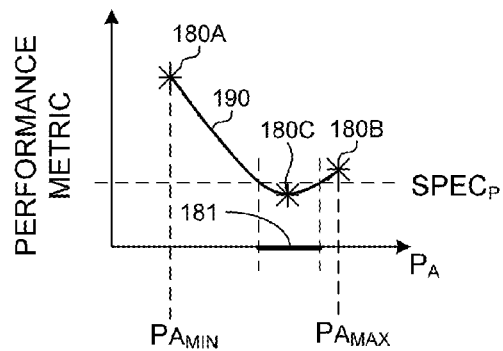
FIG. 15 illustrates a plot of measurement precision of a first metrology tool as a function of CD measurement angle parameter values, $P_A$.

FIG. 15 illustrates a plot of measurement precision of Tool A as a function of CD measurement angle parameter values, $P_A$. Minimum and maximum values ($P_{AMIN}$ and $P_{AMAX}$, respectively) are determined for CD measurement angle parameter. The minimum and maximum values could be determined based on uncertainty in factory calibration of these parameters, the physical limits of these parameters, of some other suitable approach. The middle point of the subspace of CD measurement angle is determined by a factorial design with centerpoints. The measurement precision is evaluated at the vertices (points 180A and 180B) and middle point (point 180C) of the calibration parameter subspace based on DOE data collected by Tool A. Additional points are added to the calibration parameter subspace to form a central composite design pattern. A response surface 190 associated with measurement precision is determined as a function of each point in the calibration parameter subspace. In the example depicted in FIG. 15, the response surface is a quadratic polynomial function of CD measurement angle. An operation window 181 associated with measurement precision of Tool A is determined by imposing a specification, $SPEC_P$, on response surface 190. Operation window 181 defines a range of CD measurement angle parameter values that satisfy the precision specification for Tool A.

Figure 16:
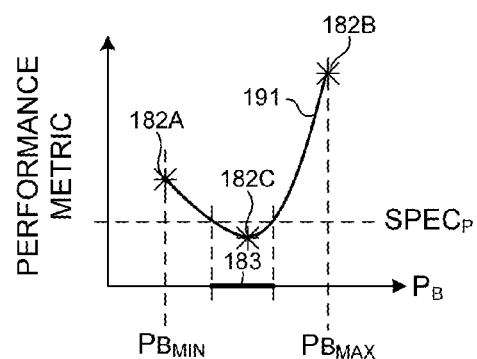
FIG. 16 illustrates a plot of measurement precision of a second metrology tool as a function of CD measurement angle parameter values, $P_B$.

FIG. 16 illustrates a plot of measurement precision of Tool B as a function of CD measurement angle parameter values, $P_B$. Minimum and maximum values ($P_{BMIN}$ and $P_{BMAX}$, respectively) are determined for CD measurement angle parameter. The measurement precision is evaluated at the vertices (points 182A and 182B) and middle point (point 182C) of the calibration parameter subspace based on DOE data collected by Tool B. Additional points are added to the calibration parameter subspace to form a central composite design pattern. A response surface 191 associated with measurement precision is determined as a function of each point in the calibration parameter subspace. In the example depicted in FIG. 16, the response surface is a quadratic polynomial function of CD measurement angle. An operation window 183 associated with measurement precision of Tool B is determined by imposing specification, $SPEC_P$, on response surface 191. Operation window 183 defines a range of CD measurement angle parameter values that satisfy the precision specification for Tool B.

A region spanned by operation windows 181 and 183 is determined. Any value of the CD measurement angle that falls within the region spanned by operation windows 181 and 183 will satisfy the measurement precision requirement. However, an optimum value of CD measurement angle is determined within the region spanned by operation windows 181 and 183 that also satisfies the matching specification.

Figure 17:
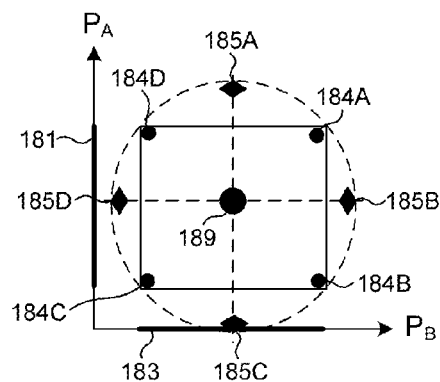
FIG. 17 illustrates a new factorial design constructed such that it completely encloses the operation windows 181 and 183 illustrated in FIGS. 15 and 16, respectively.

A matching metric is constructed, such as $MEAN((M[i][j]-M[i][k])^2)$, where the mean is evaluated over all measurements performed over the same target. The first index identifies a particular measured parameter for a particular application. The second index describes the tool. This creates a large number of individual matching metrics. FIG. 17 illustrates a new factorial design constructed such that it completely encloses the operation windows 181 and 183. The factorial design includes vertices 184A-D and centerpoint 189. A sensitivity test is employed to eliminate calibration parameters that have little impact on matching. For the remaining parameters we construct the central composite design (CCD) including added points 185A-D. Each matching metric is evaluated at the additional points in the CCD. For each matching metric a quadratic response surface model is constructed.

Figure 18:
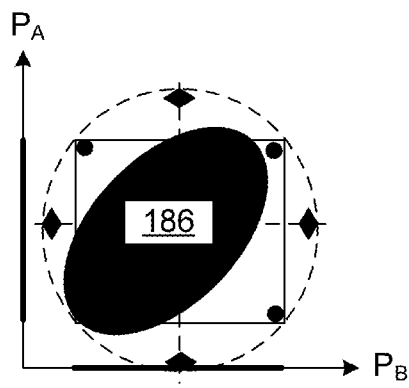
FIG. 18 illustrates the intersection of a quadratic response surface for a particular matching metric with a plane corresponding to the corresponding matching specification.
Figure 19:
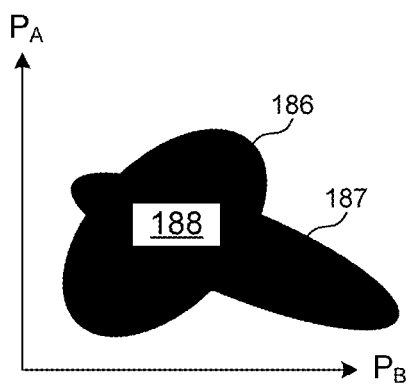
FIG. 19 illustrates the intersection of a quadratic response surface for the matching metric with a plane corresponding to the corresponding matching specification for another measurement recipe.

Based on the matching specification, an operation window for each matching metric is determined. FIG. 18 illustrates the intersection of a quadratic response surface for a particular matching metric with a plane corresponding to the corresponding matching specification. The intersection defines the operation window 186. FIG. 19 illustrates the intersection of a quadratic response surface for the matching metric with a plane corresponding to the corresponding matching specification for another measurement recipe. The intersection defines the operation window 188. The region spanned by each of these operation windows defines the overall operation window where the matching requirement is satisfied.

If the region spanned by the operation windows does not exist, or is too small, the collection of measurement recipes may be split into subgroups. Finding the operation window for these subgroups only requires re-evaluation of the regions spanned by the individual operation windows and does not require any additional computation of measured parameters. Once the overall operation window is found the optimal point in calibration parameters space can be selected that provides the desired performance for both precision and fleet matching.

As described herein, each performance metric can be considered independently. An operation window can be found for each metric, and the overall operation region can be established as the region spanned by the individual operation windows. In some examples, a single calibration that satisfies the specifications associated with the entire group of measurement applications can be found. However, if this proves to be impossible, measurements applications can be broken into subgroups with almost no additional computational effort.

Furthermore, for a quadratic polynomial response surface, most of the geometry processing associated with evaluation of operation windows and regions spanned by multiple operation windows is performed analytically. Thus, response surface approximations employing quadratic polynomial response surfaces are preferred to dramatically increase computational efficiency compared to conventional iterative optimization techniques.

In some examples, the coefficients of the response surface approximation provide information about the effect of individual calibration parameters on device performance and can be used to improve factory calibration procedures.

The methods described herein can be used to achieve higher precision, accuracy or device matching or any combination of the above, and can be applied to a single measurement or recipe. Multiple measurements can be considered at once with the overall optimum parameter window defined as the region spanned by each optimum region for individual measurements. The analysis can be performed in stages to achieve best results in minimum time. The size and configuration of DOE and the pattern selection for response surface construction can be different for each case. Pattern selections such as simple factorial, factorial with centerpoints, central composite, and fractional factorial may be contemplated. Higher order approximations may be contemplated if quadratic models prove inadequate. Depending on the order of the problem and the dimensionality of parameter space, the optimal values (or ranges) of calibration parameters can be found by analytical means (i.e. for quadratic model), iterative numeric optimization, or by a Monte-Carlo type optimization.

It may be preferable to compensate for inaccuracy introduced by the low-order response surface model by slightly tightening the target performance metrics. A step can be added at the end of the procedure to validate accuracy.

The methods described herein can be applied to proxy calibration where a proxy recipe is used to calibrate device performance for the actual production recipe.

The information captured by the response surface can be used for analysis of device performance and its connection with design and manufacturing processes, and measurement sensitivity.

Metrology systems configured to measure geometry and material properties of dielectric and metallic films and structures may employ the methods described herein. Such measurements include, by way of non-limiting example, film properties and dimensions, CD, overlay, and composition measurements. Such metrology systems may include any number of illumination sources, including, but not limited to lamps, lasers, laser driven sources, x-ray sources and euv sources. Such metrology systems may employ an number of measurement technologies, including, but not limited to all implementations of ellipsometers (including broadband spectroscopic or single wavelength, single- or multi-angle, or angle-resolved, with fixed or rotating polarizers and compensators), all implementations of reflectometers (including spectroscopic or single wavelength, single- or multi-angle, or angle-resolved), differential measurements, such as interferometers, and x-ray based metrologies.

As described herein, the term "metrology system" includes any system employed at least in part to characterize a specimen in any aspect. Exemplary terms used in the art may include a "defect inspection" system or an "inspection" system. However, such terms of art do not limit the scope of the term "metrology system" as described herein. In addition, the metrology systems 100 and 400 may be configured for inspection of patterned wafers and/or unpatterned wafers. The metrology systems may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on differences in error spectra between a reference and a target metrology tool.

Various embodiments are described herein for a semiconductor processing system (e.g., a metrology system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be "patterned" or "unpatterned." For example, a wafer may include a plurality of dies having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

A typical semiconductor process includes wafer processing by lot. As used herein a "lot" is a group of wafers (e.g., group of 25 wafers) which are processed together. Each wafer in the lot is comprised of many exposure fields from lithography processing tools (e.g. steppers, scanners, etc.). Within each field may exist multiple die. A die is the functional unit which eventually becomes a single chip. One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
    providing a first amount of illumination light to one or more structures disposed on a semiconductor wafer, the one or more structures having an unknown spectral response, the first amount of illumination light provided by an illuminator of a reference metrology system;
    detecting a first plurality of intensities of light from the one or more structures in response to the first amount of illumination light provided to the semiconductor wafer, the detected first plurality of intensities comprising a first amount of raw measurement data, the first plurality of intensities of light detected by a spectrometer of the reference metrology system;
    determining a first spectral response measurement of the one or more structures based at least in part on the first amount of raw measurement data and one or more system parameter values associated with the reference metrology system that provides the first amount of illumination light and detects the first amount of raw measurement data;
    providing a second amount of illumination light to the one or more structures disposed on the semiconductor wafer, the second amount of illumination light provided by an illuminator of a target metrology system;
    detecting a second plurality of intensities of light from the one or more structures in response to the second amount of illumination light provided to the semiconductor wafer, the detected second plurality of intensities comprising a second amount of raw measurement data, the second plurality of intensities of light detected by a spectrometer of the target metrology system;
    determining values of one or more system parameters associated with the target metrology system that provides the second amount of illumination light and detects the second amount of raw measurement data such that an error function that includes a difference between the first spectral response measurement and a second spectral response measurement of the one or more structures measured by the target metrology system is minimized, wherein the second spectral response measurement is determined based at least in part on the second amount of raw measurement data detected by the target metrology system and the values of the one or more system parameters associated with the target metrology system, wherein at least one value of at least one of the one or more system parameter values associated with the target metrology system is different from at least one value of at least one of the one or more system parameter values associated with the reference metrology system; and
    storing the values of the one or more system parameters of the target metrology system in a memory.

2. The method of claim 1, wherein the target metrology system and the reference metrology system are spectroscopic ellipsometers.

3. The method of claim 1, wherein the reference metrology system is a metrology system that performs the first spectral measurement of the one or more structures at a first time and the target metrology system is the metrology system that performs the second spectral measurement of the one or more structures at a second time after the first time.

4. The method of claim 1, wherein the determining of the values of one or more system parameters associated with the target metrology system involves a regression analysis.

5. The method of claim 1, further comprising:
    determining an estimate of a structural parameter of the one or more structures based on a regression of a reference system measurement model on the first spectral measurement; and
    determining an estimate of the structural parameter of the one or more structures based on a regression of a target system measurement model on the second spectral measurement, the target system measurement model including the values of the one or more system parameters of the target metrology system.

6. The method of claim 1, wherein the first spectral measurement of the one or more structures includes spectral measurement data associated with any of multiple measurement sites, multiple measurement samples, multiple illumination wavelengths, and multiple measurement modalities.

7. The method of claim 1, wherein the error function includes a weighted difference function including the first spectral measurement and a second spectral measurement of the one or more structures.

8. The method of claim 7, wherein the weighted difference function is based on a measurement sensitivity to any of multiple measurement sites, multiple measurement samples, multiple illumination wavelengths, and multiple measurement modalities.

9. The method of claim 7, wherein the weighted difference function is based on a measurement noise associated with any of multiple measurement sites, multiple measurement samples, multiple illumination wavelengths, and multiple measurement modalities.

10. The method of claim 1, wherein the determining the values of the one or more system parameters associated with the target metrology system involves a response surface based optimization.

11. A metrology system comprising:
    a first illuminator that provides a first amount of illumination light to one or more structures disposed on a semiconductor wafer, the one or more structures having an unknown spectral response;
    a first spectrometer that detects a first plurality of intensities of light from the one or more structures in response to the first amount of illumination light provided to the semiconductor wafer, the detected first plurality of intensities comprising a first amount of raw measurement data;
    a second illuminator that provides a second amount of illumination light to the one or more structures disposed on the semiconductor wafer;

a second spectrometer that detects a second plurality of intensities of light from the one or more structures in response to the second amount of illumination light provided to the semiconductor wafer, the detected second plurality of intensities comprising a second amount of raw measurement data; and one or more computer systems configured to:

determine a first spectral response measurement of the one or more structures based at least in part on the first amount of raw measurement data and one or more system parameter values associated with a reference metrology system that includes the first illuminator and the first spectrometer;

determine values of one or more system parameters associated with a target metrology system that includes the second illuminator and the second spectrometer such that an error function that includes a difference between the first spectral response measurement and a second spectral response measurement of the one or more structures measured by the target metrology system is minimized, wherein the second spectral response measurement is determined based at least in part on the second amount of raw measurement data detected by the target metrology system and the values of the one or more system parameters associated with the target metrology system, wherein at least one value of at least one of the one or more system parameter values associated with the target metrology system is different from at least one value of at least one of the one or more system parameter values associated with the reference metrology system; and store the values of the one or more system parameters of the target metrology system in a memory.

12. The metrology system of claim 11, wherein the first spectral measurement of the one or more structures includes spectral measurement data associated with any of multiple measurement sites, multiple measurement samples, multiple illumination wavelengths, and multiple measurement modalities.

13. The metrology system of claim 11, wherein the error function includes a weighted difference function including the first spectral measurement and a second spectral measurement of the one or more structures.

14. The metrology system of claim 13, wherein the weighted difference function is based on a measurement sensitivity to any of the multiple measurement sites, multiple measurement samples, multiple illumination wavelengths, and multiple measurement modalities.

15. The metrology system of claim 13, wherein the weighted difference function is based on a measurement noise associated with any of the multiple measurement sites, multiple measurement samples, multiple illumination wavelengths, and multiple measurement modalities.

16. The metrology system of claim 11, wherein the determining the values of the one or more system parameters associated with the target metrology system involves a response surface based optimization.

17. The metrology system of claim 11, wherein the target metrology system and the reference metrology system are spectroscopic ellipsometers.

18. The metrology system of claim 11, wherein the reference metrology system is a metrology system that performs the first spectral measurement of the one or more structures at a first time and the target metrology system is the metrology system that performs the second spectral measurement of the one or more structures at a second time after the first time.

19. The metrology system of claim 11, wherein the determining of the values of one or more system parameters associated with the target metrology system involves a regression analysis.

20. The metrology system of claim 11, the one or more computing systems further configured to:

determine an estimate of a structural parameter of the one or more structures based on a regression of a reference system measurement model on the first spectral measurement; and determine an estimate of the structural parameter of the one or more structures based on a regression of a target system measurement model on the second spectral measurement, the target system measurement model including the values of the one or more system parameters of the target metrology system.

21. A metrology system comprising:

a first illuminator that provides a first amount of illumination light to one or more structures disposed on a semiconductor wafer, the one or more structures having an unknown spectral response;

a first detector that detects a first plurality of intensities of light from the one or more structures in response to the first amount of illumination light provided to the semiconductor wafer, the first detected plurality of intensities comprising a first amount of raw measurement data;

a second illuminator that provides a second amount of illumination light to the one or more structures disposed on the semiconductor wafer;

a second detector that detects a second plurality of intensities of light from the one or more structures in response to the second amount of illumination light provided to the semiconductor wafer, the second detected plurality of intensities comprising a second amount of raw measurement data; and a non-transitory, computer-readable medium storing instructions that when executed by one or more processors causes the one or more processors to:

determine a first response measurement of the one or more structures based at least in part on the first amount of raw measurement data and one or more system parameter values associated with a reference metrology system that includes the first illuminator and the first detector;

determine values of one or more system parameters associated with a target metrology system that includes the second illuminator and the second detector such that an error function that includes a difference between the first response measurement and a second response measurement of the one or more structures measured by the target metrology system is minimized, wherein the second response measurement is determined based at least in part on the second amount of raw measurement data detected by the target metrology system and the values of the one or more system parameters associated with the target metrology system, wherein at least one value of at least one of the one or more system parameter values associated with the target metrology system is different from at least one value of at least one of the one or more system parameter values associated with the reference metrology system; and store the values of the one or more system parameters of the target metrology system in a memory.

* * * * *